United States Patent
Ji et al.

(10) Patent No.: US 8,834,846 B2
(45) Date of Patent: Sep. 16, 2014

(54) FLUORESCENT NIRF ACTIVATABLE PROBES FOR DISEASE DETECTION

(75) Inventors: Tao Ji, Hamden, CT (US); Warren M. Leevy, Granger, IN (US); William E. McLaughlin, Guilford, CT (US); Yawfui Yong, Hamden, CT (US)

(73) Assignee: Bruker Biospin Corporation, Billerica, MA (US)

( * ) Notice: Subject to any disclaimer, the term of this patent is extended or adjusted under 35 U.S.C. 154(b) by 653 days.

(21) Appl. No.: 13/101,370

(22) Filed: May 5, 2011

(65) Prior Publication Data

US 2011/0293529 A1 Dec. 1, 2011

Related U.S. Application Data

(60) Provisional application No. 61/331,885, filed on May 6, 2010.

(51) Int. Cl.
*A61B 5/00* (2006.01)

(52) U.S. Cl.
USPC .......................................................... 424/9.6

(58) Field of Classification Search
None
See application file for complete search history.

(56) References Cited

U.S. PATENT DOCUMENTS

| 5,998,146 | A | 12/1999 | Latva et al. |
| 6,329,205 | B1 | 12/2001 | Diwu et al. |
| 2004/0137475 | A1 | 7/2004 | Haugland et al. |
| 2005/0014160 | A1 | 1/2005 | Kumaraswamy et al. |
| 2005/0123957 | A1 | 6/2005 | Laitala |
| 2005/0181989 | A9 | 8/2005 | Smith et al. |
| 2006/0275775 | A1 | 12/2006 | Weissleder et al. |
| 2007/0238656 | A1 | 10/2007 | Harder et al. |
| 2008/0181965 | A1 | 7/2008 | Leon et al. |
| 2009/0061532 | A1* | 3/2009 | Papineni et al. ............... 436/501 |
| 2009/0098057 | A1 | 4/2009 | Zheng et al. |
| 2009/0209508 | A1 | 8/2009 | Lange et al. |

FOREIGN PATENT DOCUMENTS

| EP | 0 428 000 | 5/1991 |
| WO | WO97/29783 | 8/1997 |
| WO | WO2004/026344 | 4/2004 |

OTHER PUBLICATIONS

G. Volkheimer, "Persorption von Mikropartikeln," Pathologe (1993) 14, pp. 247-252, Abstract in English only.
Glen S. Kwon, et al., "Block copolymer micelles as long-circulating drug vehicles," Advanced Drug Delivery Reviews 16, (1995), pp. 295-309.
S. Moein Moghimi, et al., "Nanomedicine: current status and future prospects," The Faseb Journal, vol. 19, Mar. 2005 311-330.
A.J. Khopade, et al., "Targeting of multiple emulsions to the lungs," Pharmazie, 51 (1996) 8, pp. 558-562.
Vinod Labhasetwar, et al., "Nanoparticle drug delivery system for restenosis," Advanced Drug Delivery Reviews 24 (1997), pp. 63-85.
Mamoru Yamashita MD, PhD, et al., "Mist Particle Diameters are Related to the Toxicity of Waterproofing, Sprays: Comparison Between Toxic and Non-Toxic Products," Vet Human Toxicol, 39 (2) Apr. 1997, pp. 71-74.
Benoit Dubertret, et al., "Single-mismatch detection using gold-quenched fluorescent oligonucleotides," Nature Biotechnology, vol. 19, Apr. 2001, pp. 365-370.
Jixiang Liu, et al. "Fluorescent Molecular Probes V: A Sensitive Caspase-3 Substrate for Fluorometric Assays," Bioorganic & Medicinal Chemistry Letters, 9 (1999), pp. 3231-3236.
Judie B. Alimonti, et al., "Granzyme B Induces BID-mediated Cytochrome *c* Release and Mitochondrial Permeability Transition," The Journal of Biological Chemistry, vol. 276, No. 10, Mar. 2001, pp. 6974-6982.
Barry G. Rosser, et al., "Calpain Activity Increases in Hepatocytes Following Addition of ATP," The Journal of Biological Chemstry, vol. 268, No. 31, Nov. 1993, pp. 23593-23600.
M. Sharon Stack, et al., "Comparison of Vertebrate Collagenase and Gelatinase Using a New Fluorogenic Substrate Peptide," The Journal of Biological Chemistry, vol. 264, No. 8, Mar. 1989, pp. 4277-4281.
Gerard M. McGeehan, et al., "Characterization of the Peptide Substrate Specificities of Interstitial Collagenase and 92-kDa Gelatinase," The Journal of Biological Chemistry, vol. 269, No. 52, Dec. 1994, pp. 32814-32820.
C. Graham Knight, et al., "A novel coumarin-labelled peptide for sensitive continuous assays of the matrix metalloproteinases," FEBS, vol. 296, No. 3, Jan. 1992, pp. 263-266.
Hideaki Nagase, et al., "Design and Characterization of a Fluorogenic Substrate Selectively Hydrolyzed by Stromelysin 1 (Matrix Metalloproteinase-3)," The Journal of Biological Chemistry, vol. 269, No. 33, Aug. 1994, pp. 20952-20957.
J. Oliver McIntyre, et al., "Development of a novel fluorogenic proteolytic beacon for in vivo detection and imaging of tumour-associated matrix metalloroteinase-7 activity," Biochem. J., 2004, 377, pp. 617-628.
Anthony R. Welch, et al., "Purification of Human Matrilysin Produced in *Escherichia coli* and Characterization Using a New Optimized Fluorogenic Peptide Substrate," Archives of Biochemistry and Biophysics, vol. 324, No. 1 Dec. 1995, pp. 59-64.
Steven J. Kridel, et al., "Substrate Hydrolysis by Matrix Metalloproteinase-9," The Journal of Biological Chemistry, vol. 276, No. 23, Jun. 2001, pp. 20572-20578.
Hollis R. Williams, et al., "Human Polymorphonuclear Leukocyte Collagenase and Gelatinase," Int. J. Biochem., vol. 16, No. 12, 1984, pp. 1321-1329.

(Continued)

*Primary Examiner* — Paul Dickinson
(74) *Attorney, Agent, or Firm* — O'Shea Getz P.C.

(57) ABSTRACT

Fluorescent activatable probes for imaging biological processes and disease detection in vitro and in vivo. There is also described a method for detecting the presence of an enzyme. A sample is contacted with a nanoparticle including a monomer, at least one cleavable spacer comprising at least one fluorescence activation site, and at least two dyes of at least two types. The cleavable spacer is attached at one end to the nanoparticle. The at least two types comprise an energy donor type and an energy acceptor type. At least one dye of one type is embedded in the nanoparticle and the cleavable spacer has at least one dye of the other type attached. The at least two dyes comprise at least one matched pair capable of fluorescence resonance energy transfer. Fluorescence is detected by exposing the sample to a light source, and detecting emitted light with a detector.

20 Claims, 7 Drawing Sheets

(56) References Cited

OTHER PUBLICATIONS

Vera Knäuper, et al., "Biochemical Characterization of Human Collagenase-3," The Journal of Biological Chemistry, vol. 271, No. 3, Jan. 1996, pp. 1544-1550.

Su-Jun Deng, et al., "Substrate Specificity of Human Collagenase 3 Assessed Using a Phage-displayed Peptide Library," The Journal of Biological Chemistry, vol. 275, No. 40, Oct. 2000, pp. 31422-31427.

Gary S. Coombs, et al., "Directing Sequence-specific Proteolysis to New Targets," The Journal of Biological Chemistry, vol. 273, No. 8, Feb. 1998, pp. 4323-4328.

Song-Hua Ke, et al., "Distinguishing the Specificities of Closely Related Proteases," The Journal of Biological Chemistry, vol. 272, No. 26, Jun. 1997, pp. 16603-16609.

Dirk T.S. Rijkers, et al., "Design and Synthesis of Thrombin Substrates with Modified Kinetic Parameters," Thrombosis Research, vol. 79, Nos. 5/6, Sep. 1995, 491-499.

Bradley J. Backes, et al., "Synthesis of positional-scanning libraries of fluorogenic peptide substrates to define the extended substrate specificity of plasmin and thrombin," Nature Biotechnology, vol. 18, Feb. 2000, pp. 187-193.

Jennifer L. Harris, et al., "Rapid and general profiling of protease specificity by using combinatorial fluorogenic substrate libraries," PNAS, vol. 97, No. 14, Jul. 2000, pp. 7754-7759.

Umar Mahmood, et al., "Near-Infrared Optical Imaging of Proteases in Cancer," Molecular Cancer Therapeutics, vol. 2, May 2003, pp. 489-496.

Sudhir Agrawal, et al., "Site specific functionalization of oligonucleotides for attaching two different reporter groups," Nucleic Acids Research, vol. 18, No. 18, Jun. 1990, pp. 5419-5423.

Sommay Soukchareun, et al., "Preparation and Characterization of Antisense Oligonucleotide—Peptide Hybrids Containing Viral Fusion Peptides," Bioconjugate Chem., 1995, 6, pp. 43-53.

Khalil Arar, et al., "Synthesis and Antiviral Activity of Peptide—Oligonucleotide Conjugates Prepared by Using $N_a$-(Bromoacetyl)peptides," Bioconjugate Chem., 1995, 6, pp. 573-577.

G. Köhler, et al., "Derivation of specific antibody-producing tissue culture and tumor lines by cell fusion," Eur. J. Immunol., 1976, 6, pp. 511-519.

Greg Winter, et al., "Man-made antibodies," Nature, vol. 349, Jan. 1991, pp. 293-299.

Albert F. LoBuglio, et al., "Mouse/human chimeric monoclonal antibody in man: Kinetics and immune response," Proc. Natl. Acad. Sci., vol. 86, Jun. 1989, pp. 4220-4224, Immunology.

* cited by examiner

1ST COLUMN = ACTIVATABLE PROBES LIVER, SKIN, TUMOR, PANCREAS, SPLEEN
2ND COLUMN = ACTIVATABLE PROBES GI, KIDNEYS, LUNGS, HEART
3RD COLUMN = CONTROL PROBES LIVER, SKIN, TUMOR, PANCREAS, SPLEEN
4TH COLUMN = CONTROL PROBES GI, KIDNEY, LUNG, HEART

FLUORESCENT NIRF ACTIVATABLE PROBES FOR DISEASE DETECTION

CROSS-REFERENCE TO RELATED APPLICATIONS

This is a 111(a) application of and claims priority to Provisional Application Ser. No. 61/331,885, filed May 6, 2010, incorporated herein by reference.

This application claims priority to commonly assigned, co-pending U.S. patent application Ser. No. 11/732,424, filed on Apr. 3, 2007 entitled "LOADED LATEX OPTICAL MOLECULAR IMAGING PROBES", incorporated herein by reference in its entirety.

This application claims priority to commonly assigned, co-pending U.S. patent application Ser. No. 12/201,190, filed on Aug. 29, 2009 entitled "FLUORESCENCE RESONANCE ENERGY TRANSFER DETECTION WITH NANOPARTICLES FOR IN VITRO AND IN VIVO APPLICATIONS", incorporated herein by reference in its entirety.

This application claims priority to commonly assigned, co-pending U.S. patent application Ser. No. 11/872,866, filed on Oct. 16, 2007 entitled "SILICA-CORED CARRIER PARTICLE", incorporated herein by reference.

This application claims priority to commonly assigned, co-pending U.S. patent application Ser. No. 13/043,057, filed on Mar. 8, 2011, entitled "LOADED LATEX OPTICAL MOLECULAR IMAGING PROBES CONTAINING LIPOPHILIC LARGE STOKES SHIFT DYES", incorporated herein by reference.

This application claims priority to commonly assigned, co-pending U.S. patent application Ser. No. 11/712,531, filed on Aug. 28, 2008, entitled "LARGE STOKE SHIFT DYE USED FOR OPTICAL IMAGING", incorporated herein by reference.

FIELD OF THE INVENTION

The invention relates generally to the field of optical molecular imaging, and in particular, to fluorescent particles for biological assays, particularly as fluorescent activatable probes for optical molecular imaging. More specifically, the invention relates to fluorescent activatable probes for the imaging of biological processes and disease detection in vitro and in vivo.

BACKGROUND OF THE INVENTION

Optically based biomolecular assay techniques such as optical microtiter plate reading and optical molecular imaging are powerful tools for studying the temporal and spatial dynamics of specific biomolecules and their interactions in real time in vitro and in vivo. These techniques have been increasingly used to probe protein function and gene expression. Optically based techniques exhibit advantages of picosecond temporal resolution which is important for functional imaging, submicron spatial resolution, in vivo microscopy, single molecule sensitivity and other minimally invasive techniques. These techniques also offer the potential for simultaneous use of multiple and distinguishable probes in molecular imaging. By eliminating ionizing radiation, these techniques also offer safety. These techniques have advanced over the past decade due to rapid developments in laser technology, sophisticated reconstruction algorithms and imaging software originally developed for non-optical, tomographic imaging modes such as CT and MRI.

Of the various optical imaging techniques investigated to date, near-infrared fluorescence (NIRF) imaging is of particular interest for non-invasive in vivo imaging because of the relatively low tissue absorbance, minimal autofluorescence of near-infrared (NIR) light, and deep tissue penetration of up to 6-8 centimeters. In near-infrared fluorescence imaging, a laser or appropriately filtered light is used as a source of fluorescence excitation. The excitation light travels through body tissues. When it encounters a near-infrared fluorescent molecule ("contrast agent" or "probe"), the excitation light is absorbed. The fluorescent molecule then emits light as fluorescence with a longer wavelength and therefore spectrally distinguishable from the excitation light. Despite good penetration of biological tissues by near-infrared light, conventional near-infrared fluorescence probes are subject to many of the same limitations encountered with other contrast agents, including low signal-to-noise ratios.

A number of NIRF contrast-enhanced optical imaging probes have been developed and evaluated in small animals. These studies have established the use of near-infrared optical imaging in diagnosis, molecular characterization, and monitoring of treatment response in a number of disease models. Nanoparticles have been increasingly used in a wide range of biomedical applications such as drug carriers and imaging agents. They are engineered materials with dimensions typically smaller than 100 nm, which are small enough to reach almost anywhere in the body. These nanoparticles can be derivatized with a variety of targeting ligands, multiple imaging moieties for multiple modalities imaging, or loaded with multiple molecules of a contrast agent, providing a significant boost in signal intensity for diverse imaging modalities. NIRF imaging based on nanoparticulate imaging probes is rapidly emerging as an advanced technology for noninvasive cancer detection, diagnostic and therapeutic applications. Because small probes are subjected to fast excretion in vivo, given internal clearance of small molecules and reticuloendothelial system clearance of non-immunologically shielded compounds, nanoparticle-based imaging probes offer potential advantages over small molecule or other low molecular weight polymer-based probes.

The principle of detection by fluorescence resonance energy transfer (FRET), also known as Förster resonance energy transfer (FRET), resonance energy transfer (RET), and electronic energy transfer (EET), is based on the transfer of energy from an excited donor dye to an acceptor dye or quenchers that are located in spatial proximity. Dark acceptors or quenchers are substances that absorb excitation energy from a fluorophore and dissipate the energy as heat; while fluorescent acceptors or quenchers re-emit much of this energy as light. FRET can be used to determine distance at a molecular level in a range between approximately 1 to 10 nm because the efficiency E of the energy transfer is very sensitive to the distance R between the donor species and acceptor species and declines proportionally to $R_0^6/(R_0^6+R^6)$, where $R_0$ is the material-specific Förster radius defined as the distance at which the efficiency is 50%, and typically lies in the range of a few nanometers (less than approximately 10 nm). Depending on the fluorescence quantum efficiency of the acceptor species, the energy transferred from the donor species to the acceptor species can either undergo nonradiative relaxation by means of internal conversion thereby leading to quenching of the donor energy, or can be emitted by means of fluorescence of the acceptor species.

FRET occurs between the electronic excited states of the donor species and acceptor species when they are in sufficient proximity to each other, in which the excited-state energy of the donor species is transferred to the acceptor species. The result is a decrease in the lifetime and a quenching of fluorescence of the donor species. In one application of this principle, a fluorescent moiety is caused to be in close proximity to a quencher moiety. In this configuration, the energy from the excited donor fluorescent moiety is transferred to the acceptor quencher moiety and dissipated as heat rather than fluorescence.

The use of fluorescence resonance energy transfer (FRET) labels in biological systems is known. The principle has been used in the detection of binding events or cleavage reactions in assays employing fluorescence resonance energy transfer. In the case of peptide cleavage reactions, a fluorescent donor dye and fluorescent acceptor dye may be attached to a peptide substrate on either side of the peptide bond to be cleaved and at such a distance that non-radiative energy transfer between the donor and the acceptor species takes place. For example, EP 0428000 discloses a novel fluorogenic peptide substrate involving a fluorescent donor molecule and a quenching acceptor molecule attached thereto. The labeled substrate can be used in the detection and assay of a viral protease enzyme, whereby, if there is enzyme present in a test sample, the substrate is cleaved and the donor and acceptor species are thereby separated. The resultant fluorescent emission of the donor species can be measured.

In biological systems, FRET is used to detect the mutual spatial proximity of appropriately labeled biomolecules or particles. FRET can be used as a method for detecting protein-protein interactions, e.g., as a method for detecting an antigen-antibody reaction, a receptor-ligand interaction, a nucleic acid hybridization, hormone-receptor interaction or the binding of proteins to nucleic acids. The detection is itself effected by means of measuring the change in the intensity of, or the spectral change in, the donor fluorescence or acceptor fluorescence, or by means of measuring a change in the decay time of the donor fluorescence. While such systems may have achieved certain degrees of success in their particular applications, there remains a need for an activatable imaging probe with a suitable signal-to-noise ratio for use in vivo and in vitro.

SUMMARY OF THE INVENTION

An object of the present invention relates to a nanoparticle comprising a monomer represented by the formula:

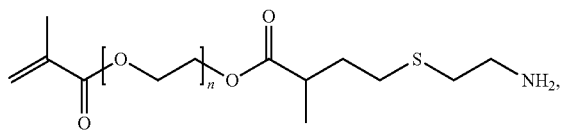

where n is 10 to 200, at least one cleavable spacer comprising at least one fluorescence activation site, wherein the cleavable spacer is attached at one end to the nanoparticle, and at least two dyes of at least two types, wherein the at least two types comprise an energy donor type and an energy acceptor type, wherein at least one dye of one type is embedded in the nanoparticle and the cleavable spacer has at least one dye of the other type attached, and wherein the at least two dyes comprise at least one matched pair capable of fluorescence resonance energy transfer.

Another object of the invention relates to a nanoparticle comprising a latex material, wherein the latex material comprises, a mixture represented by formula: (X)m-(Y)n-(Z)o-(W)p, wherein Y is at least one monomer with at least two ethylenically unsaturated chemical functionalities; Z is at least one polyethylene glycol macromonomer with an average molecular weight of between 300 and 10,000; W is an ethylenic monomer different from X, Y, or Z; and X is at least one water insoluble, alkoxethyl containing monomer represented by formula:

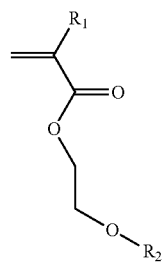

wherein R1 is a radical chosen from the group consisting of methyl and hydrogen, and R2 is a radical chosen from the group consisting of an alkyl group and an aryl group; and m, n, o, and p are weight percent ranges of each component monomer, wherein m ranges between 40-90 percent by weight, n ranges between 1-10 percent by weight, o ranges between 20-60 percent by weight, and p is up to 10 percent by weight, at least one fluorescence activation site, and at least two dyes of at least two types, wherein the at least two types comprise an energy donor type and an energy acceptor type, wherein the at least two dyes comprise at least one matched pair capable of fluorescence resonance energy transfer, and wherein fluorescence activation may be induced by enzymatic cleavage of fluorescence activation sites.

Another object of the present invention relates to a method for detecting the presence of an enzyme, comprising the steps of: contacting a sample with a nanoparticle comprising a monomer represented by formula:

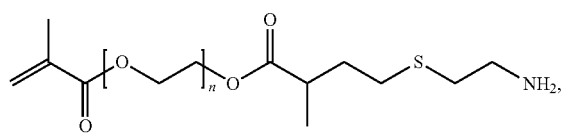

where n is 10 to 200, at least one cleavable spacer comprising at least one fluorescence activation site, wherein the cleavable spacer is attached at one end to the nanoparticle, and at least two dyes of at least two types, wherein the at least two types comprise an energy donor type and an energy acceptor type, wherein at least one dye of one type is embedded in the nanoparticle and the other end of the spacer has at least one dye of the other type attached, wherein the at least two dyes comprise at least one matched pair capable of fluorescence resonance energy transfer, and detecting fluorescence by exposing the sample to a light source and detecting emitted light with a detector.

DETAILED DESCRIPTION OF THE INVENTION

The present invention relates to a nanoparticle-based imaging probe comprising a nanoparticle, for example a latex nanoparticle (also referred to as a nanolatex particle). In one embodiment, the nanoparticle comprises a fluorescent dye compound; a cleavable spacer comprising at least one fluorescence activation site; and a quencher dye compound. The imaging probe emits substantial fluorescence only after activation, for example, after interaction with a target enzyme or tissue. This increases the signal-to-noise ratio by several orders of magnitude and enables near-infrared fluorescence imaging of the sample, for example, internal target tissues in vivo, based on enzymatic activity present in the sample. Accordingly, an embodiment of the invention features a fluorescence-quenched probe comprising a nanoparticle, loaded with at least one near infrared dye.

In another embodiment, the fluorescence-quenching is caused by energy transfer from the near infrared fluorophore to a quencher. The nanoparticle can comprise a nanolatex particle. Fluorescence activation may be induced by enzymatic cleavage of an attachment moiety, for example, a cleavable spacer.

Nanoparticles used in accordance with the invention may be in the form of a biological cargo-laden nanoparticle(s) as described in copending, commonly assigned U.S. patent application Ser. No. 11/732,424 filed on Apr. 3, 2007, by Leon et al entitled "LOADED LATEX OPTICAL MOLECULAR IMAGING PROBES" and in previously mentioned U.S. patent application Ser. No. 11/400,935 by Harder et al. In such nanoparticles, fluorescence quenching may be caused by energy transfer from the near-infrared fluorophore to a quencher. Fluorescence activation may be induced by enzymatic cleavage at fluorescence activation sites.

Figure 1:
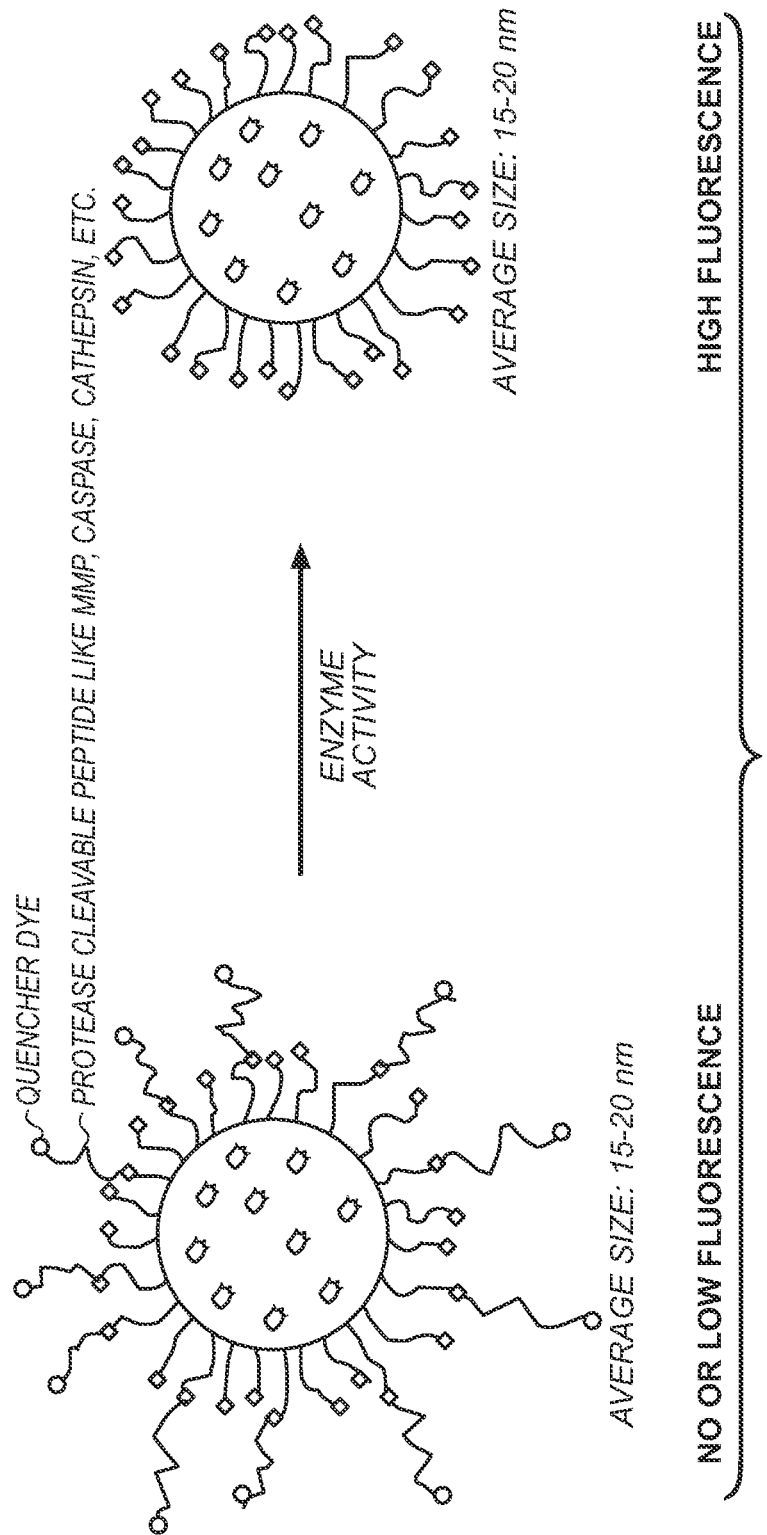
FIG. 1 is an illustration of a fluorescent activatable probe of the present invention.

One activation scheme is illustrated in FIG. 1. The quencher dyes may be attached to a loaded nanoparticle via an attachment moiety having at least one fluorescence activation site, for example, an enzyme-specific or sensitive peptide. Upon enzymatic cleavage (such as by MMP-2) of the attachment moiety, the quencher dyes, along with peptide fragment, are released from the imaging probe leading to increased fluorescence. In another activation scheme, the quencher dye is loaded into the nanolatex and the fluorescent dye is attached via the cleavable spacer groups to the nanolatex particle (quenched state). The fluorescent dye fluoresces (activated state) once it is released from the nanolatex particle by cleavage.

In one embodiment, the invention also features an in vivo optical imaging method. The method includes: (a) administering to a living animal or human a fluorescence-quenched probe comprising fluorescence activation sites activatable by enzymatic cleavage that accumulates preferentially in a target tissue; (b) allowing time for (1) the probe to accumulate preferentially in the target tissue, and (2) enzymes in the target tissue to activate the probe by enzymatic cleavage at fluorescence activation sites, if the target tissue is present; (c) illuminating the target tissue with near infrared light of a wavelength absorbable by the fluorescent dyes; and (d) detecting fluorescence emitted by the fluorescent dyes.

The above method can be used, e.g., for in vivo or in vitro imaging of a tumor in a human patient or a sample (specimen), or in vivo detection or evaluation of arthritis in a joint of a human patient. The invention also features an in vivo method for selectively imaging at least two different cells or tissue types simultaneously. The method includes administering, to an animal or human patient, at least two different fluorescence-quenched probes, each of which accumulates preferentially in a target tissue. Each of the at least two probes includes fluorescence activation sites. The probes are activatable by enzymatic cleavage and each of the at least two probes comprises a fluorescent dye whose fluorescence wavelength is distinguishable from that of the other fluorescent dye, and each of the at least two probes contains a different activation site.

Whenever used in the specification the terms set forth shall have the following meaning:

The term "fluorescence activation site" means a covalent bond within a probe, which bond is: (1) cleavable by an enzyme present in a target tissue or sample, and (2) located so that its cleavage liberates a dye from being held in a fluorescence-quenching position.

The term "fluorescence-quenched" means energy donor dyes and energy acceptor dyes are attached or loaded into (directly or indirectly through a spacer) the nanoparticle so that the energy donor dyes and energy acceptor dyes are maintained in a position relative to each other that permits them to interact photochemically and quench the fluorescence from the energy donor dyes.

For purposes of the present invention: "PEGylated" refers to nanolatex compositions which are composed of at least 5 weight percent covalently bound poly(ethylene glycol). "Pegylation" typically refers to the reaction by which a PEG-protein/peptide conjugate is obtained starting from the activated PEG and the corresponding protein/peptide. This may also apply to PEG-Therapeutic Agent, PEG-Dye, PEG-bioligand, PEG-(MRI Contrast Agent), PEG-(X-Ray Contrast Agent), PEG-Antibody, PEG-(Enzyme Inhibitor) PEG-(radioactive isotope), PEG-(quantum dot), PEG-oligosaccharide, PEG-polygosaccharide, PEG-hormone, PEG-dextran, PEG-oligonucleotide, PEG-carbohydrate, PEG-neurotransmitter, PEG-hapten, and PEG-carotinoid.

"Nanolatex" refers to a hydrophobic polymer particle which has a hydrodynamic diameter of less than 100 nm.

A "water dispersible crosslinked polymer particle" refers to a polymer particle which is a contiguous, crosslinked polymer network through which a through-bond path can be traced between any two atoms (not including counter ions) in the particle. The particle is capable of existing in water in such a state of division that each individual particle network is separated from every other by the aqueous continuous phase.

A "hydrophobic crosslinked polymer" refers to a polymer consisting of at least 45 weight percent of water-insoluble monomers. The polymer is a contiguous network through which a through-bond path can be traced between any two atoms (not including counter ions).

"Biocompatible" means that a composition does not disrupt the normal function of the bio-system into which it is introduced. Typically, a biocompatible composition will be compatible with blood and does not otherwise cause an adverse reaction in the body. For example, to be biocompatible, the material should not be toxic, immunogenic or thrombogenic.

"Colloidally stable" refers to the state in which the particle is capable of existing in aqueous phosphate buffered saline (137 mM NaCl, 2.7 mM KCl, 10 mM $Na_2HPO_4$, 2 mM $KH_2PO_4$ at pH 7.4.) in such a state of division that that each individual particle is separated from every other by the aqueous continuous phase without the formation of agglomerates (entities comprising multiple individual particles in intimate contact) or without bulk flocculation occurring.

"Loaded" or "embedded" refers to a non-covalent association between the dye and the polymer particle such that when the latex is dispersed in water at a concentration of less than 10%, less than 1% of the total dye in the system can be extracted into the water continuous phase.

"Sample" refers to a specimen which can be obtained from an animal, such as a human. The sample can be analyzed using the methods and compositions of the present invention.

In one embodiment, the latex of this invention is composed of repetitive crosslinked ethylenically unsaturated monomers. The latex may have a volume-average hydrodynamic diameter ranging from about 5 to about 100 nm, preferably 8 to 50 nm as determined by quasi-elastic light scattering in phosphate buffered saline (137 mM NaCl, 2.7 mM KCl, 10 mM $Na_2HPO_4$, 2 mM $KH_2PO_4$ at pH 7.4). In one embodiment, the activatable probes of the invention may have a volume-average hydrodynamic diameter of about 12 nm to about 24 nm, preferably about 15 nm to about 20 nm. In another embodiment, the probes have a hydrodynamic diameter of about 12 nm. In a third embodiment, the probes have a hydrodynamic diameter of about 24 nm.

A loaded nanolatex particle useful for the present invention relates to hydrophobic infrared dyes non-covalently loaded into heavily PEGylated nanolatex particle. When used in IR-active assemblies, these loaded nanolatex particles show highly efficient fluorescence, low dye aggregation, and high photostability, that is, are less subject to bleaching. These assemblies are also non-cytotoxic and are colloidally very stable, that is, are less prone to aggregation.

In one embodiment, the loaded latex particle of the invention comprises a latex material made from a mixture represented by the following Formula I:

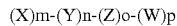  FORMULA I wherein X is at least one water insoluble, alkoxethyl containing monomer; Y is at least one monomer with at least two ethylenically unsaturated chemical functionalities; Z is at least one polyethylene glycol macromonomer with an average molecular weight of between 300 and 10,000; W is an ethylenic monomer different from X, Y, or Z. The weight percent range of each component monomer is represented by m, n, o, and p: m ranges between 40-90 wt %, preferably from 45-60 wt %; n ranges between 1-10 wt %, preferably 2-6 wt %; o ranges between 20-60 wt %, preferably between 40-50 wt %; and p is up to 10 wt %.

In Formula I, X is a water-insoluble, alkoxyethyl-containing monomer described below by Formula 2. In Formula 2, R1 is methyl or hydrogen. R2 is an alkyl or aryl group containing up to 10 carbons. Preferably, X is methoxyethyl methacrylate or alkoxyethyl acrylate.

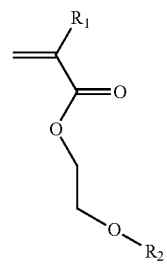

FORMULA 2

In Formula 1, Y is a water-insoluble or water-soluble monomer containing at least two ethylenically unsaturated chemical functionalities. These functionalities may be vinyl groups, acrylates, methacrylates, acrylamides, methacrylamides, allyl groups, vinyl ethers and vinyl esters. Y monomers include, but are not necessarily limited to aromatic divinyl compounds such as divinylbenzene, divinylnaphthalene or derivatives thereof, diethylene carboxylate esters and amides such as ethylene glycol dimethacrylate, diethylene glycol diacrylate, 1,4 butanediol diacrylate, 1,4 butanediol dimethacrylate, 1,3 butylene glycol diacrylate, 1,3 butylene glycol dimethacrylate, cyclohexane dimethanol diacrylate, cyclohexane dimethanol dimethacrylate, diethylene glycol diacrylate, diethylene glycol dimethacrylate, dipropylene glycol diacrylate, dipropylene glycol dimethacrylate, ethylene glycol diacrylate, ethylene glycol dimethacrylate, 1,6 hexanediol diacrylate, 1,6 hexanediol dimethacrylate, neopentyl glycol diacrylate, neopentyl glycol dimethacrylate, tetraethylene glycol diacrylate, tetraethylene glycol dimethacrylate, triethylene glycol diacrylate, triethylene glycol dimethacrylate, tripropylene glycol diacrylate, tripropylene glycol dimethacrylate, pentaerythritol triacrylate, trimethylolpropane triacrylate, trimethylolpropane trimethacrylate, dipentaerythritol pentaacrylate, di-trimethylolpropane tetraacrylate, pentaerythritol tetraacrylate, divinyl esters such as divinyl adipate, and other divinyl compounds such as divinyl sulfide or divinyl sulfone compounds of allyl methacrylate, allyl acrylate, cyclohexanedimethanol divinyl ether diallylphthalate, diallyl maleate, dienes such as butadiene and isoprene and mixtures thereof.

The W monomer can comprise any other inert monomers which are added to modify the properties. W is a non-chemically reactive monomer which can be added in small amounts to impart desired properties to the latex, such as water dispersibility, charge, more facile dye loading, or to make the latex more hydrophobic. For example, W may be a water-soluble monomer such as 2-phosphatoethyl acrylate potassium salt, 3-phosphatopropyl methacrylate ammonium salt, vinylphosphonic acid, and their salts, vinylcarbazole, vinylimidazole, vinylpyrrolidone, vinylpyridines, acrylamide, methacrylamide, maleic acid and salts thereof, sulfopropyl acrylate and methacrylate, acrylic and methacrylic acids and salts thereof, N-vinylpyrrolidone, acrylic and methacrylic esters of alkylphosphonates, styrenics, acrylic and methacrylic monomers containing amine or ammonium functionalities, styrenesulfonic acid and salts thereof, acrylic and methacrylic esters of alkylsulfonates, vinylsulfonic acid and salts thereof, vinylpyridines, hydroxyethyl acrylate, glycerol acrylate and methacrylate esters, (meth)acrylamide, and N-vinylpyrrolidone. W may alternately be a water-insoluble monomer such as methyl methacrylate, ethyl methacrylate, isobutyl methacrylate, 2-ethylhexyl methacrylate, benzyl methacrylate, cyclohexyl methacrylate and glycidyl methacrylate, acrylic/acrylate esters such as methyl acrylate, ethyl acrylate, isobutyl acrylate, 2-ethylhexyl acrylate, benzyl methacrylate, phenoxyethyl acrylate, cyclohexyl acrylate, and glycidyl acrylate, styrenics such as styrene, a-methylstyrene, ethylstyrene, 3- and 4-chloromethylstyrene, halogen-substituted styrenes, and alkyl-substituted styrenes, vinyl halides and vinylidene halides, N-alkylated acrylamides and methacrylamides, vinyl esters such as vinyl acetate and vinyl benzoate, vinyl ether, allyl alcohol and its ethers and esters, and unsaturated ketones and aldehydes such as acrolein and methyl vinyl ketone, isoprene, butadiene and acrylonitrile.

Z is a polyethylene glycol macromonomer with a molecular weight of between 300 and 10,000, preferably between 500 and 5000. In one embodiment, Z is a polyethylene glycol macromonomer represented by a general formula:

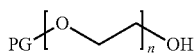

wherein n is greater than 4 and PG is a polymerizable group.

In one embodiment, Z is a linking polymer. Preferably, the linking polymer is a polyethylene glycol backbone chain with specific functional end groups at each end, which allows the polyethylene glycol to act as a linking group between two materials through the two functional end groups.

Preferably, the polyethylene glycol macromonomer contains a radical polymerizeable group at one end. This group can be, but is not necessarily limited to a methacrylate, acrylate, acrylamide, methacrylamide, styrenic, allyl, vinyl, maleimide, or maleate ester. Preferably, the polyethylene glycol macromonomer additionally contains a reactive chemical functionality at the other end which can serve as an attachment point for other chemical units, such as quenchers or antibodies. This chemical functionality may be, but is not limited to alcohols, thiols, carboxylic acids, primary or secondary amines, vinylsulfonyls, aldehydes, epoxides, hydrazides, succinimidyl esters, maleimides, a-halo carbonyl moieties (such as iodoacetyls), isocyanates, isothiocyanates, and aziridines. Preferably, these functionalities will be carboxylic acids, primary amines, maleimides, vinylsulfonyls, or secondary amines.

A class of polyethylene glycol macromonomers with a reactive functional group at one end is described by Formula 3.

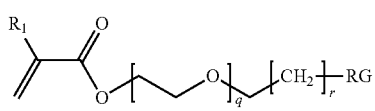

FORMULA 3

In Formula 3, R1 is hydrogen or methyl, q is 10-200, r is 0-10, and RG is a hydrogen or reactive chemical functionality which can be a alcohol, thiol, carboxylic acid, primary or secondary amine, vinylsulfonyl, aldehyde, epoxy, hydrazide, succinimidyl ester, maleimide, a substituted or unsubstituted acetate, or substituted carbamyl, substituted phosphate, substituted or unsubstituted sulfonate a-halo carbonyl moiety (such as iodoacetyl), isocyanate, isothiocyanate, or aziridine.

In one embodiment, the linking polymer is utilized in two different ways. First, a single linking polymer may be used to attach one functional compound of interest to another, thereby producing a single compound with two different desired functions. Multiple linking polymers may also be attached to a single large particle or bead at one end and a compound of interest on the other, thereby producing a single carrier particle for a large payload of functional compound of interest.

In another embodiment, the linking polymer may be used in both the acylation and alkylation approaches and is compatible with aqueous and organic solvent systems, so that there is more flexibility in reacting with useful groups and the desired products are more stable in an aqueous environment, such as a physiological environment. Preferably, the linking polymer has at least two reactive groups, one of which is an acrylate which is useful for forming nanogels and latexes and reacting with thiols through Michael addition; the other reactive groups are useful for conjugation to contrast agents, dyes, proteins, amino acids, peptides, antibodies, bioligands, therapeutic agents and enzyme inhibitors. The linking polymer may be branched or unbranched. Preferably, for therapeutic use of the end-product preparation, the linking polymer will be pharmaceutically acceptable.

RG in Formula 3 is hydrogen or a reactive chemical functionality. Preferably, the reactive chemical functionality allows the loaded latex to be covalently bonded to a biomolecule and the location of the biomolecule can be determined by fluorescent imaging. The covalent attachment provides a link that is stable to handling, changes in solvent, pH, and ionic strength, and temperature. This stable association between the loaded latex particle and the biomolecule is important to insure that the fluorescent signal that is detected relates to the presence of the biomolecule. If a loaded latex is not covalently attached and associated with the biomolecule through ionic attraction, or Van der Waals forces, then the dye may become detached and the desired biomolecule signal will decrease and false signals may be obtained from the separated loaded latex such that the fluorescence image does not indicate the location of the biomolecule. Alternatively, the reactive chemical functionality (RG) will allow covalent bonding to occur in organic solvents such as N,N-dimethylformamide, dimethylsulfoxide, N-methylpyrrolidone, and non-organic solvents such as water.

In yet another embodiment, the reactive chemical functionality (RG) will allow the use of linkers that are designed to form covalent bonds between the reactive chemical functionality (RG) on the loaded latex and an attachment group on a bio molecule such as an amine, alcohol, carboxylic acid or thiol from amino acids, peptides, protein, cells, RNA, DNA or other linkers which have been added to the biomolecule to allow for greater flexibility in the methods used to attach biomolecules to other materials. Such linkers would include but not be limited to hetero-bifunctional or homo-bifunctional linkers such as bis-sulfosuccinylsuberate, 3-[2-(aminoethyl)dithio]propionic acid, p-azidobenzoylhydrazide, bis-maleimidohexane, N-succinimidyl-S-acetylthioacetate, N-Sulfosuccinimidyl-4-azidophenyl-1-3'-dithiopropionatte, Succinimidyl 4-[p-maleimidophenyl]butyrate, N-Succinimidyl[4-iodoacetyl]aminobenzoate, Sulfosuccinimidyl-[perfluoroazidobenzamido]ethyl-1,3'-dithiopropionate, Succinimidyl 3-[bromoacetamido]propionate, Sulfosuccinimidyl 2-[7-amino-4-methylcoumarin-3-acetamido]ethyl-1, 3'dithiopropionate, 3-(2-Pyridyldithio)propionyl hydrazide), N-e-Maleimidocaproyloxy]succinimide ester, N-[4-(p-Azidosalicylamido)butyl]-3'-(2'-pyridyldithio)propionamide, Succinimidyl 4-[N-maleimidomethyl]cyclohexane-1-carboxylate, 4-(4-N-Maleimidophenyl)butyric acid hydrazide hydrochloride, Disuccinimidyl suberate, Lomant's Reagent, Sulfosuccinimidyl[2-6-(biotinamido)-2-(p-azidobenzamido)-hexanoamido]-ethyl-1,3'-dithiopropionate, β-[Tris(hydroxymethyl)phosphino]propionic acid (betaine), (Sulfosuccinimidyl 4-[p-maleimidophenyl]butyrate), Bis- Maleimidoethane, Bis-[b-(4-Azidosalicylamido)ethyl] disulfide, Succinimidyl 4-[N-maleimidomethyl] cyclohexane-1-carboxy-[6-amidocaproate], N-[p-Maleimidophenyl]isocyanate, m-Maleimidobenzoyl-N-hydroxysulfosuccinimide ester, Sulfosuccinimidyl 4-N-maleimidomethyl cyclohexane-1-carboxylate, Bis[sulfosuccinimidyl]suberate, N-[g-Maleimidobutyryloxy] sulfosuccinimide ester, N-succinimidyl 4-pentynoate, and N-succinimidyl 4-azidoylbutanoate.

The reactive chemical functionality may also serve as an attachment point for a metal chelating group used to chelate metals such as radioisotopes (for PET imaging) and Gadolinium (for MRI) imaging. In one embodiment, the metal chelating group is S-2-(4-Isothiocyanatobenzyl)-1,4,7,10 tetraazododecane-tetraacetic acid or 2-(4-Isothiocyanatobenzyl)diethylenetriaminepentaacetic acid. The metal chelating group may be bound to a radioisotope or heavy metal.

The reactive chemical functionality (RG) on the loaded latex can be covalently attached to any drug or biomolecule in such a way to optimize the fluorescent signal and not interfere with the normal function of the biomolecule. Preferably, the carboxylic acid attachment group can be converted to an active ester to enable the covalent bond formation. An N-hydroxysuccinimide ester is a preferred method of activating the carboxylic acid group. The carboxylic acid attachment group can also be activated for covalent bond formation with carbodiimide reagents such as dicylcohexylcarbodiimide. A hydroxyl attachment group can be activated for covalent bond formation by forming a chloroformate such as p-nitrophenyl chloroformate. An amine attachment group can be activated for covalent bond formation by forming using the carbodiimide activating agent to react with carboxylic acid functions of the biomolecule, or forming isocyanates or isothiocyanates or using an amine reactive linking group from the list above. The maleimide linking group can react with thiol groups typically available from cysteine residues in biomolecules or a thiol linking group from the list above, an isocyanate or isothiocyanate can be used directly to react with amine groups of a biomolecule. The trialkoxysilane can be used to react with other trialkoxysilanes or siloxide modified molecules or particles. The alkyne and azidoyl group can be used to form a stable triazole link often catalyzed by copper (I); such that if the dye contains an alkynyl attachment group, then an azidoyl attachment group is placed on the biomolecule or the opposite where an azidoyl group is the attachment group on the dye and an alkynyl group is added to the biomolecule.

A preferred water-soluble linking polymer for use herein is a polyethylene glycol derivative of Formula 4. Polyethylene glycol (PEG) is a hydrophilic, biocompatible and non-toxic polymer of general formula $H(OCH_2CH_2)_nOH$, wherein $n > 4$.

FORMULA 4

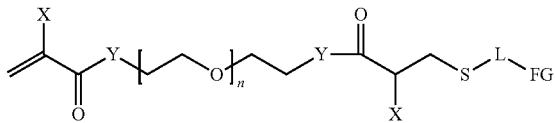

wherein $X=CH_3$ or H, $Y=O$, NR, or S, L is a linking group or spacer, FG is a functional group, n is greater than 4 and less than 1000. Most preferably, $X=CH_3$, $Y=O$, NR, L is alkyl or aryl, and FG is $NH_2$ or COOH, and n is between 6 and 500 or between 10 and 200; more preferably, $n=16$.

In one embodiment, the linking polymer may be used by attaching to biologically important materials, dyes, antibodies and contrast agents for detection of disease and the study of metabolic activity, therapeutic agents for the treatment of disease, agents for making thickener agents, pharmaceuticals, and cosmetics. The biologically important materials for attachment of the linking polymer include targeting agents, diagnostic agents, and therapeutic agents, which can be greatly improved in effectiveness when linked.

The dyes useful for imaging probes of the present invention may be either attached to the nanolatex particle or loaded into the nanolatex. The dyes can include both fluorescent dyes and quencher dyes.

In one embodiment, the loaded dyes are fluorescent dyes and their quantum efficiency can be enhanced. Dyes such as cyanine dyes tend to form aggregates that do not fluoresce and fluorescence quantum yield decreases. Loading the dye in to the nanolatex can reduce the aggregation and thus improve quantum efficiency. In one such embodiment, quencher dyes are attached via the cleavable spacer groups to the nanolatex particle. The fluorescence of the nanoparticle is quenched (quenched state) via fluorescence resonance energy transfer (FRET) between the donor fluorescent dye and acceptor quencher dye provided they are in close proximity. The imaging probe fluoresces (activated state) after the quencher dye is released from the polymer shell of the nanoparticle by enzyme specific cleavage.

In one embodiment, the loaded dyes are quencher dyes and fluorescent dyes are attached via the cleavable spacer groups to the nanolatex particle (quenched state). The fluorescent dye fluoresces (activated state) once it is released from the nanolatex particle by cleavage.

Fluorescent dye compounds suitable for use in the present invention can include a single molecule or molecular dye. Dyes useful for this invention include fluorescent, hydrophobic dyes that fluoresce in a range from 400 to 1000 nm. Classes of dyes include, but are not necessarily limited to oxonol, pyrylium, Squaric, croconic, rodizonic, polyazaindacenes or coumarins, scintillation dyes (usually oxazoles and oxadiazoles), aryl- and heteroaryl-substituted polyolefins ($C_2$-$C_8$ olefin portion), merocyanines, carbocyanines, phthalocyanines, oxazines, carbostyryl, porphyrin dyes, dipyrrometheneboron difluoride dyes aza-dipyrrometheneboron difluoride dyes, and oxazine dyes. Commercially available fluorescent dyes useful in the invention are listed in Table 1. Useful dyes are carbocyanine, phthalocyanine, or aza-dipyrrometheneboron difluoride.

TABLE 1

Commercially available fluorescent dyes.

5-Amino-9-diethyliminobenzo(a)phenoxazonium Perchlorate
7-Amino-4-methylcarbostyryl
7-Amino-4-methylcoumarin
7-Amino-4-trifluoromethylcoumarin
3-(2'-Benzimidazolyl)-7-N,N-diethylaminocoumarin
3-(2'-Benzothiazolyl)-7-diethylaminocoumarin
2-(4-Biphenylyl)-5-(4-t-butylphenyl)-1,3,4-oxadiazole
2-(4-Biphenylyl)-5-phenyl-1,3,4-oxadiazole
2-(4-Biphenyl)-6-phenylbenzoxazole-1,3
2,5-Bis-(4-biphenylyl)-1,3,4-oxadiazole
2,5-Bis-(4-biphenylyl)-oxazole
4,4'''-Bis-(2-butyloctyloxy)-p-quaterphenyl
p-Bis(o-methylstyryl)-benzene
5,9-Diaminobenzo(a)phenoxazonium Perchlorate
4-Dicyanomethylene-2-methyl-6-(p-dimethylaminostyryl)-4H-pyran
1,1'-Diethyl-2,2'-carbocyanine Iodide
1,1'-Diethyl-4,4'-carbocyanine Iodide
3,3'-Diethyl-4,4',5,5'-dibenzothiatricarbocyanine Iodide
1,1'-Diethyl-4,4'-dicarbocyanine Iodide
1,1'-Diethyl-2,2'-dicarbocyanine Iodide TABLE 1-continued Commercially available fluorescent dyes.

3,3'-Diethyl-9,11-neopentylenethiatricarbocyanine Iodide
1,3'-Diethyl-4,2'-quinolyloxacarbocyanine Iodide
1,3'-Diethyl-4,2'-quinolylthiacarbocyanine Iodide
3-Diethylamino-7-diethyliminophenoxazonium Perchlorate
7-Diethylamino-4-methylcoumarin
7-Diethylamino-4-trifluoromethylcoumarin
7-Diethylaminocoumarin
3,3'-Diethyloxadicarbocyanine Iodide
3,3'-Diethylthiacarbocyanine Iodide
3,3'-Diethylthiadicarbocyanine Iodide
3,3'-Diethylthiatricarbocyanine Iodide
4,6-Dimethyl-7-ethylaminocoumarin
2,2'''-Dimethyl-p-quaterphenyl
2,2''-Dimethyl-p-terphenyl
7-Dimethylamino-1-methyl-4-methoxy-8-azaquinolone-2
7-Dimethylamino-4-methylquinolone-2
7-Dimethylamino-4-trifluoromethylcoumarin
2-(4-(4-Dimethylaminophenyl)-1,3-butadienyl)-3-ethylbenzothiazolium Perchlorate
2-(6-(p-Dimethylaminophenyl)-2,4-neopentylene-1,3,5-hexatrienyl)-3-methylbenzothiazolium Perchlorate
2-(4-(p-Dimethylaminophenyl)-1,3-butadienyl)-1,3,3-trimethyl-3H-indolium Perchlorate
3,3'-Dimethyloxatricarbocyanine Iodide
2,5-Diphenylfuran
2,5-Diphenyloxazole
4,4'-Diphenylstilbene
1-Ethyl-4-(4-(p-Dimethylaminophenyl)-1,3-butadienyl)-pyridinium Perchlorate
1-Ethyl-2-(4-(p-Dimethylaminophenyl)-1,3-butadienyl)-pyridinium Perchlorate
1-Ethyl-4-(4-(p-Dimethylaminophenyl)-1,3-butadienyl)-quinolium Perchlorate
3-Ethylamino-7-ethylimino-2,8-dimethylphenoxazin-5-ium Perchlorate
9-Ethylamino-5-ethylamino-10-methyl-5H-benzo(a)phenoxazonium Perchlorate
7-Ethylamino-6-methyl-4-trifluoromethylcoumarin
7-Ethylamino-4-trifluoromethylcoumarin
1,1',3,3,3',3'-Hexamethyl-4,4',5,5'-dibenzo-2,2'-indotricarboccyanine Iodide
1,1',3,3,3',3'-Hexamethylindodicarbocyanine Iodide
1,1',3,3,3',3'-Hexamethylindotricarbocyanine Iodide
2-Methyl-5-t-butyl-p-quaterphenyl
3-(2'-N-Methylbenzimidazolyl)-7-N,N-diethylaminocoumarin
2-(1-Naphthyl)-5-phenyloxazole
2,2'-p-Phenylen-bis(5-phenyloxazole)
3,5,3'''',5'''''-Tetra-t-butyl-p-sexiphenyl
3,5,3'''',5'''''-Tetra-t-butyl-p-quinquephenyl
2,3,5,6-1H,4H-Tetrahydro-9-acetylquinolizino-<9,9a,1-gh> coumarin
2,3,5,6-1H,4H-Tetrahydro-9-carboethoxyquinolizino-<9,9a,1-gh> coumarin
2,3,5,6-1H,4H-Tetrahydro-8-methylquinolizino-<9,9a,1-> coumarin
2,3,5,6-1H,4H-Tetrahydro-9-(3-pyridyl)-quinolizino-<9,9a,1-gh> coumarin
2,3,5,6-1H,4H-Tetrahydro-8-trifluoromethylquinolizino-<9,9a,1-gh> coumarin
2,3,5,6-1H,4H-Tetrahydroquinolizino-<9,9a,1-gh> coumarin
3,3',2'',3'''-Tetramethyl-p-quaterphenyl
2,5,2'''',5'''''-Tetramethyl-p-quinquephenyl
P-terphenyl
P-quaterphenyl
Nile Red
Rhodamine 700
Oxazine 750
Rhodamine 800
IR 125
IR 144
IR 140
IR 132
IR 26
IR 5
Diphenylhexatriene
Diphenylbutadiene
Tetraphenylbutadiene
Naphthalene
Anthracene TABLE 1-continued Commercially available fluorescent dyes.

Pyrene
Chrysene
Rubrene
Coronene
Phenanthrene
Fluorene
Aluminum phthalocyanine
Platinum octaethylporphyrin Additional dyes useful in the present invention include Dye 1, Dye 2, Dye 3, and Dye 4 shown below

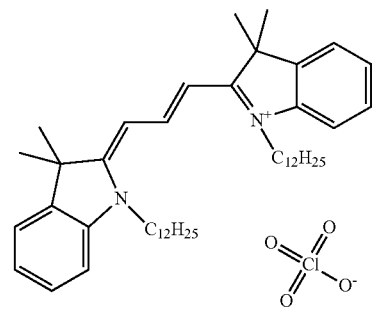

Dye 1

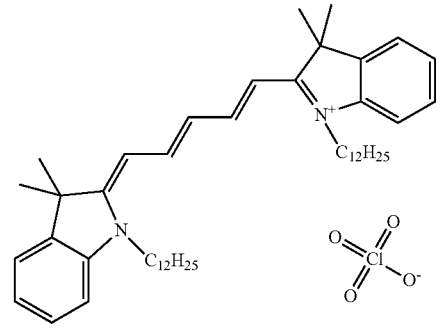

Dye 2

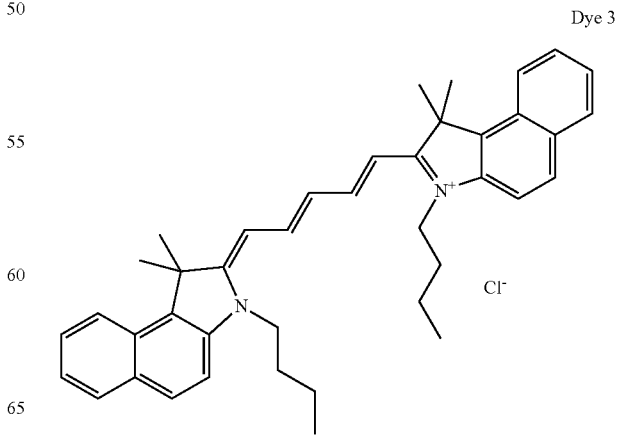

Dye 3

Dye 4

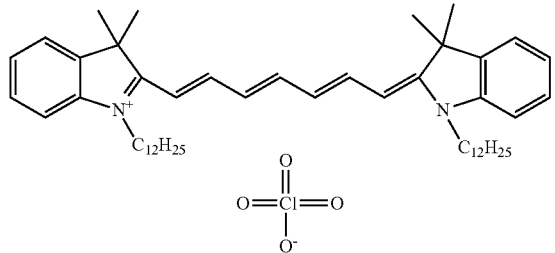

Dyes further useful for this invention are fluorescent dyes with large Stokes shift which are organic solvent soluble and demonstrate insolubility in water. When the dyes are loaded into the water soluble latex particle, an increase is observed in quantum yield of fluorescence as compared to the quantum yield of the dye in aqueous solvent. The present invention relates to a fluorescent activatable probe comprising a water dispersible, near-infrared tricarbocyanine, enamine-functionalized dye having a Stokes shift of greater than 50 nm and represented by the following two general formulae:

General Formula I

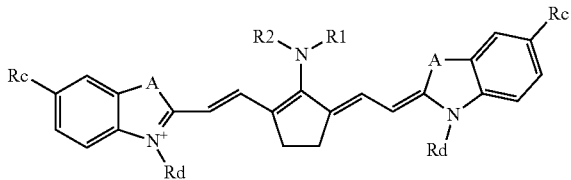

wherein R1 and R2 are substituted alkyl and may form a ring; A is NRa, S, O, Ra—C—Rb, wherein Ra and Rb are substituted or unsubstituted alkyl groups capable of forming a ring; Rc is hydrogen, aryl, alkyl, alkoxy, or halogen; Rd is alkyl chain CH2(n)-CH3 where n=2 to 30, and/or aryl group; a preferred embodiment comprises the case wherein Rd is alkyl where n=11; and General Formula II

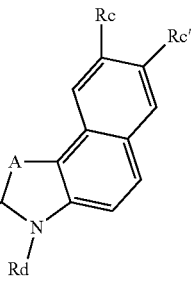

wherein R1 and R2 are substituted alkyl and are capable of forming a ring; A is NRa, S, O, Ra—C—Rb, wherein Ra and Rb are substituted or unsubstituted alkyl groups capable of forming a ring; Rc is hydrogen, aryl, alkyl, alkoxy, or halogen; Rd is alkyl chain CH2(n)-CH3 where n=2 to 30, and/or aryl group.

The excitation and emission wavelengths of the dyes incorporated in the particles should be selected such that the fluorescence measurement is not confounded due to the sample that is being visualized. For example, when the sample is human blood serum, the donor should not comprise a dye whose maximum absorption is below 500 nm where human blood serum has high absorption and some fluorescence emission. The brightness of a fluorescent dye is the product of the extinction coefficient and the fluorescence quantum yield of the dye. Therefore dyes should be chosen which have high extinction coefficients and high fluorescence quantum yields. The same desire for high extinction coefficients and fluorescence quantum yields is seen in a bright particle that contains multiple molecules of the same or similar dyes. For organic florescent dyes the difference between the absorption maximum and the emission maximum is termed the "Stokes shift". Cyanine dyes typically have a Stokes shift of 20-40 nm, and more typically around 20 nm, and are examples of organic dyes with red or near-infrared absorption and emission maxima that possess high extinction coefficients. In order to obtain efficient fluorescence-quenching, the dye absorption and emission properties of the donor dyes and the acceptor dyes are preferably carefully chosen to comprise a matched pair capable of fluorescence resonance energy transfer. The emission spectrum of the donor dye should overlap with the absorption spectrum of the acceptor dye. Consequently the acceptor dye absorption maximum will always be lower in energy, i.e., higher in wavelength, than the donor dye absorption maximum.

The size of the nanoparticulate assemblies is another significant parameter in determining their usefulness in biological compositions. After administration in the body, large particles are eliminated by the reticuloendothelial system and cannot be easily transported to the disease site. See, for example, Volkheimer, Pathologe 14:247 (1993); Kwon and Kataoka, Adv. Drug. Del. Rev. 16:295 (1995); Moghimi et al., "Nanomedicine: Current Status and Future Prospects." FASEB Journal 2005, 19, 311-330. Particles larger than 100 nm are susceptible to clearance by interstitial macrophages while particles of 150 nm or larger are susceptible to accumulation in the liver. Also, the transport of large particles in the cell and intracellular delivery is limited or insignificant. See, for example, Labhasetwar et al., Adv. Drug Del. Res. 24:63 (1997). It was demonstrated that an aggregated cationic species with a size from 500 nm to over 1 micron are ineffective in cell transfection. Large particles, particularly, those positively charged exhibit high toxicity in the body, in part due to adverse effects on liver and embolism. See, for example, Volkheimer, Pathologe 14:247 (1993); Khopade et al Pharmazie 51:558 (1996); Yamashita et al., Vet. Hum. Toxicol, 39:71 (1997).

Particles with hydrophobic composition will improve dye photostability and brightness. Particles with hydrophilic composition will improve biodistribution and blood circulation time. Other methods have tried to solve the need for both water-soluble and water-insoluble properties of a particle with a core/shell structure where a central core is water-insoluble, the surrounding shell is water-soluble, and the fluorescent molecules are contained in the core. Many fluorescent nanoparticles known today are made of fluorescent metals such as lanthanides and cadmium/selenium that are water-insoluble and also exhibit toxicity and poor biodistribution. In order to overcome these defects, methods have been employed to create a water-soluble polymer shell around the metal nanoparticle or insoluble core. However, these polymer shells increase the diameter of the nanoparticles which can affect the biodistribution of the nanoparticle. The methods and compositions of the present invention exhibit desired biodistribution.

In one embodiment of this invention, the biological or pharmaceutical component of interest is attached to the fluorescent activatable probe by reaction with a reactive chemical unit at the terminus of the highly hydrophilic macromonomer units. This reactive chemical unit may be an amine. Most preferably, this attachment occurs via a linking polymer.

The fluorescent activatable probes can serve to easily identify whether enzymes are present on specific tissues or cells in vivo or in vitro. The fluorescent activatable probes can be visualized by cell imaging systems, specific tissue imaging systems, drug delivery systems, etc. A suitable system for fluorescent detection by imaging, i.e., detection at multiple, spatially distributed points, is an Image Station 4000MM Pro commercially available from Carestream Health, Inc., of Rochester, N.Y. The 4000MM Pro system has a broad-spectrum, i.e., white light source, such as a xenon light source, along with a set of excitation filters. The excitation filters preferred are bandpass interference filters which can transmit light in selected spectral bands, for example a filter with 520 nm central wavelength that transmits light inside a spectral band from 510 nm to 530 nm but blocks all the light outside this spectral band from reaching the sample. For measuring emission, the preferred instrument utilizes a second set of bandpass interference filters that pass the emission light from the fluorescent activatable probe but blocks the excitation light and other fluorescent signals. The preferred instrument has a digital camera, preferably comprising a cooled CCD detector, that has high sensitivity between 500 nm and 900 nm, and a computer and software to display the captured image. The preferred system is capable of receiving a sample disposed in a microtiter plate.

Another suitable system, such as an In-Vivo Imaging System FX Pro, also commercially available from Carestream Health, Inc., is capable of fluorescent activatable probe detection by imaging a living small animal, such as a mouse. Still another suitable system for fluorescent activatable probe detection is a microtiter plate reader, such as the SpectraMax M5 commercially available from Molecular Devices, of Sunnyvale, Calif., which uses a photomultiplier tube for sequential fluorescence detection from individual wells. An individual of ordinary skill in the art would recognize the equivalence of sequential fluorescent activatable probe detection using a microtiter plate reader and fluorescent activatable probe detection by imaging using a digital camera. The SpectraMax M5 also uses monochromators for in both the excitation light source and the detector. An individual of ordinary skill in the art would recognize that monochromators have similar capability of spectral selectivity as interference filters. Another suitable system for fluorescent activatable probe detection is a microfluidics system, such as achieved by RainStorm™ droplet-based microfluidics technology commercially available from RainDance Technologies, Inc., of Lexington, Mass. An individual of ordinary skill in the art would recognize the equivalence of fluorescent activatable probe detection from a sample disposed in a microfluidic droplet and fluorescent activatable probe detection in a sample disposed in a microtiter plate.

Many dyes do not emit fluorescent light because excitation energy is emitted as heat or non-fluorescent light. Of those dyes that do emit fluorescent energy, many are self quenched due to aggregation effects or have low quantum yields. These dyes may be used as quencher dyes.

The fluorescent activatable probes of the present invention are optically silent (quenched, no fluorescence) in their native (quenched) state and become highly fluorescent after enzyme-mediated release of dyes. Quencher dye compounds suitable for use in the present invention can include a single molecule or molecular dye (U.S. Pat. No. 6,329,205B1), gold cluster (Dubertret B, Calame M, and Libchaber A J, Nat. Biotechnol. 2001; 19: 365-70), carbon nanotube, or nanoparticle dyed with light absorbing molecules. Selection of quencher labels is explained in U.S. Pat. No. 5,998,146 and US 2005/0123957. Suitable quencher dyes include e.g. DABCYL and QSY-series from Molecular Probes (www.probes.com), Dark Cy-dyes from Amersham Biosciences (www.amershambiosciences.com), Eclipse Dark Quencher dyes from Epoch Biosciences (www.epochbio.com), Black Hole Quencher dyes from Biosearch Technologies (www.biosearchtech.com), DYQ-dyes from Dyomics (www.dyomics.com), Black Berry Quenchers from Berry & Associates (www.berryassoc.com), and ElleQuencher from Oswel (www.oswel.com). Additional quencher dye compounds suitable for use in the present invention are represented by the following formula:

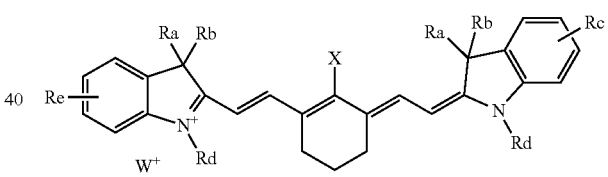

wherein X is Cl, or aryl-substituted S, O, or N; Ra and Rb are substituted or unsubstituted alkyl and may form a ring; Rc is hydrogen or $SO_3^-$, aryl, alkyl, alkoxy, or halogen and may form a fused ring with indole; and Rd is substituted or unsubstituted alkyl. At least one of the substituents is a linking group selected from a list of OH, COOH, $NH_2$, $Si(OEt)_3$, $N_3$, terminal alkyne, maleimide, thiol, isocyanate, isothiocyanate.

The following are some specific examples for such quencher molecules:

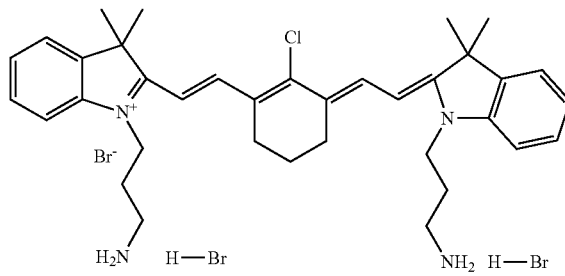 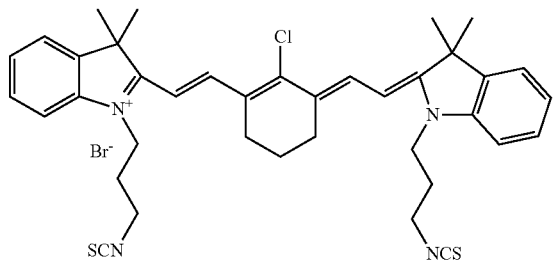

-continued
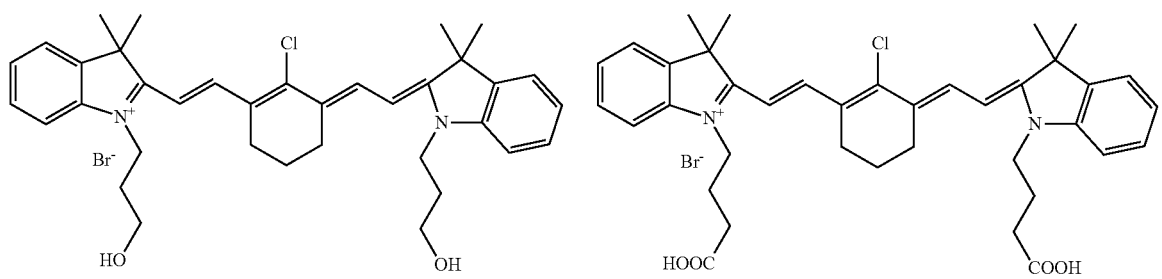
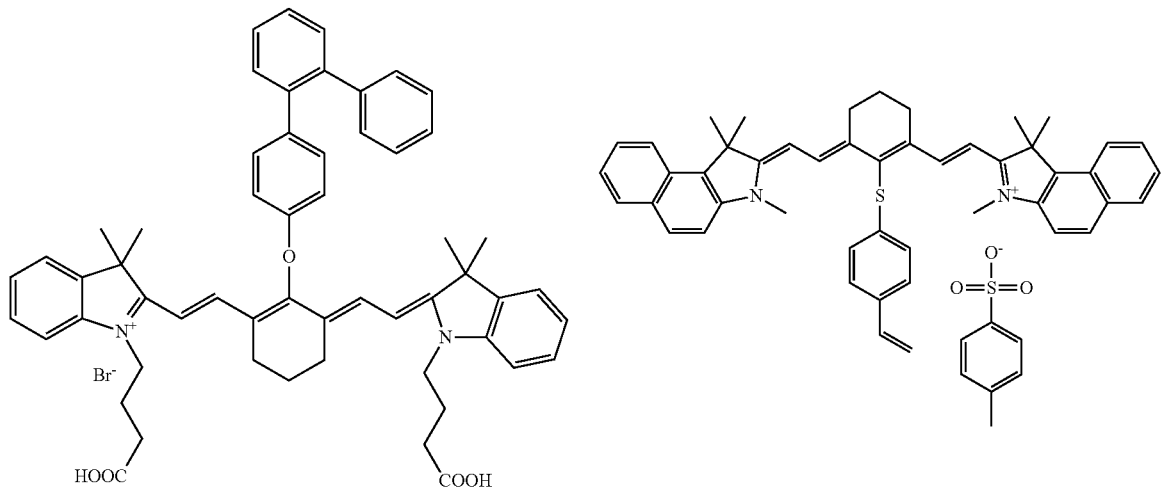
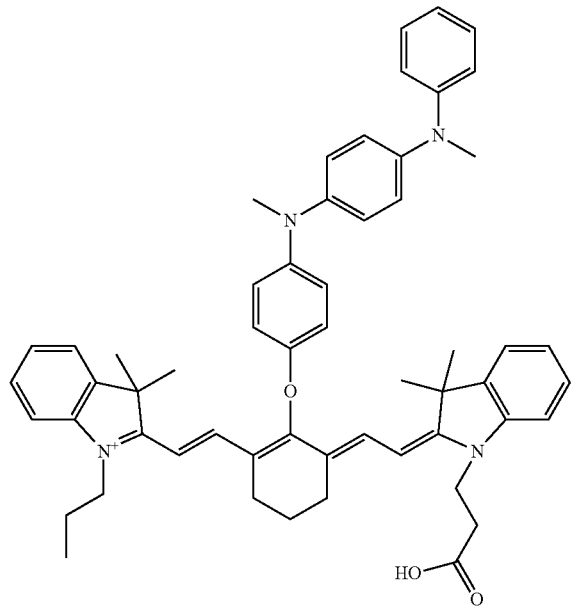

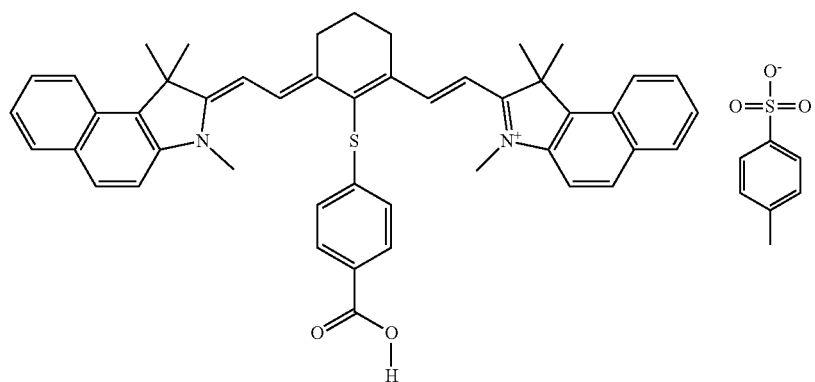
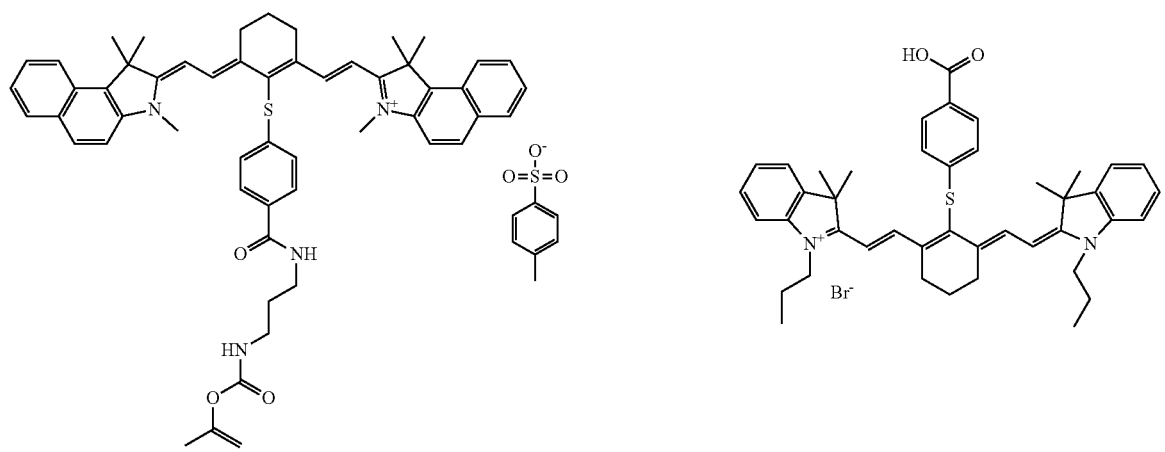
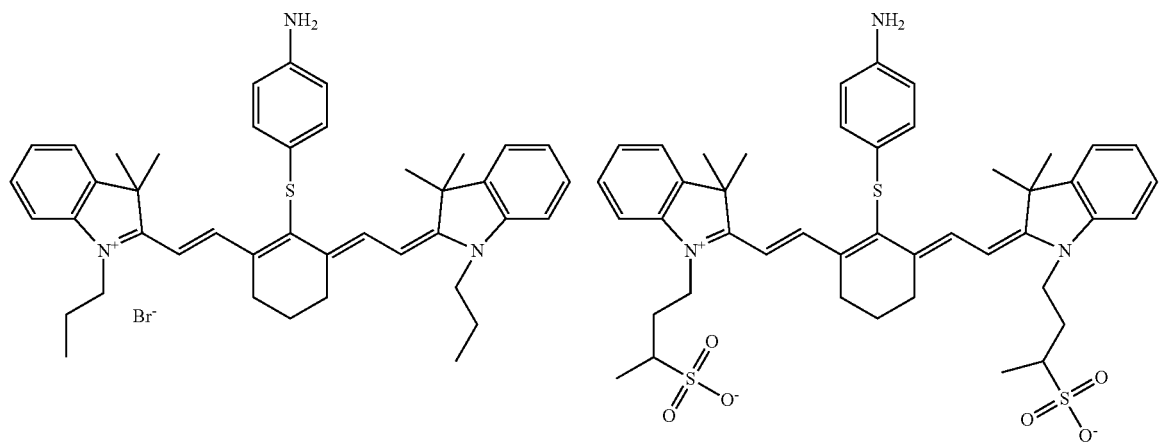

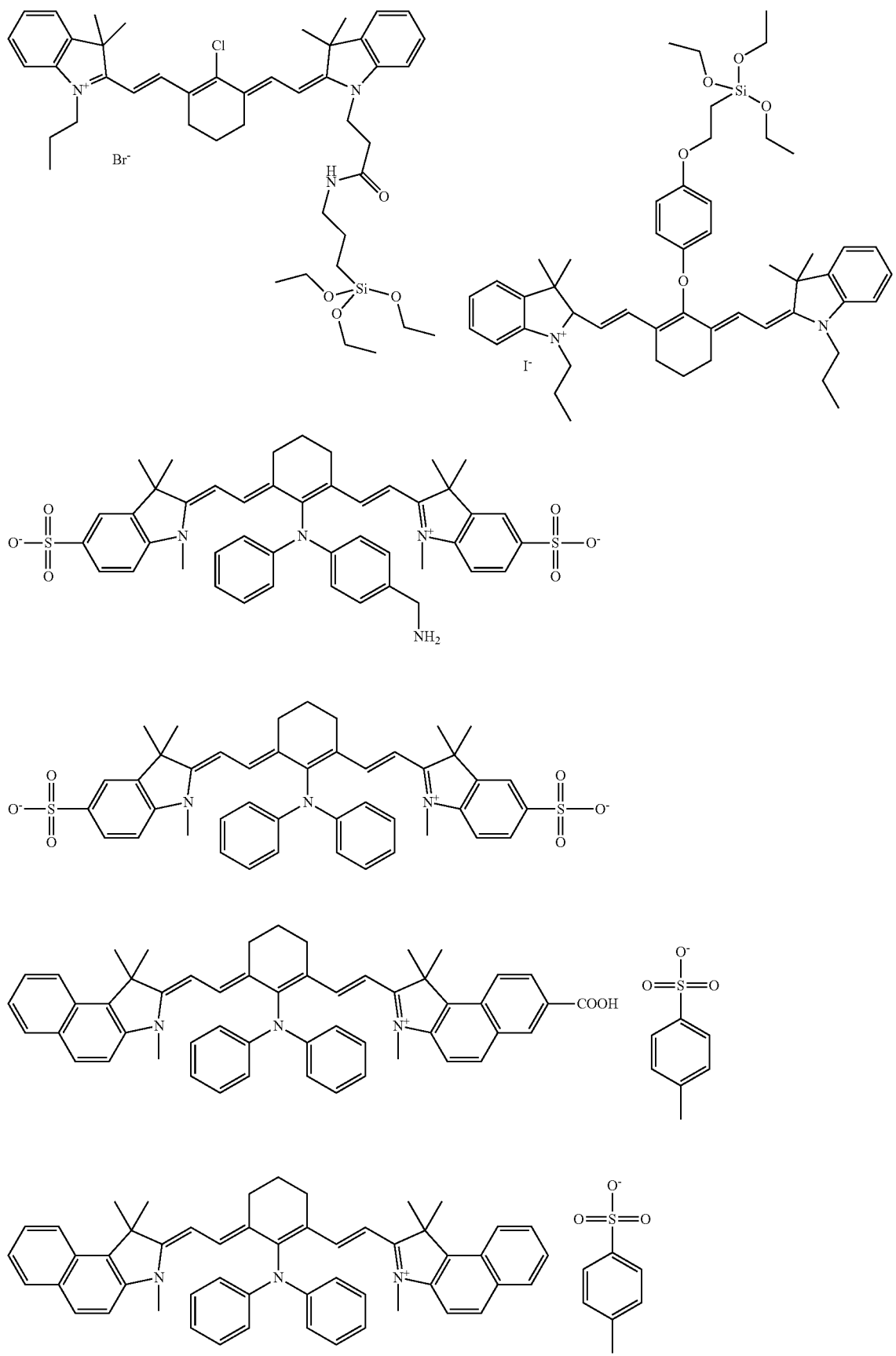

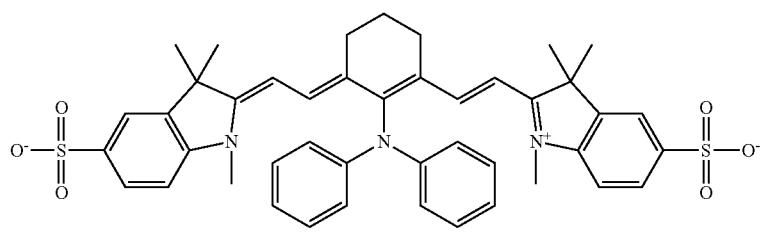
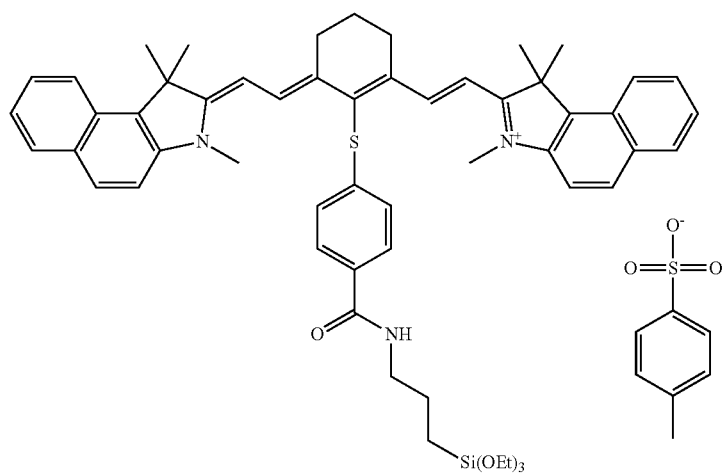
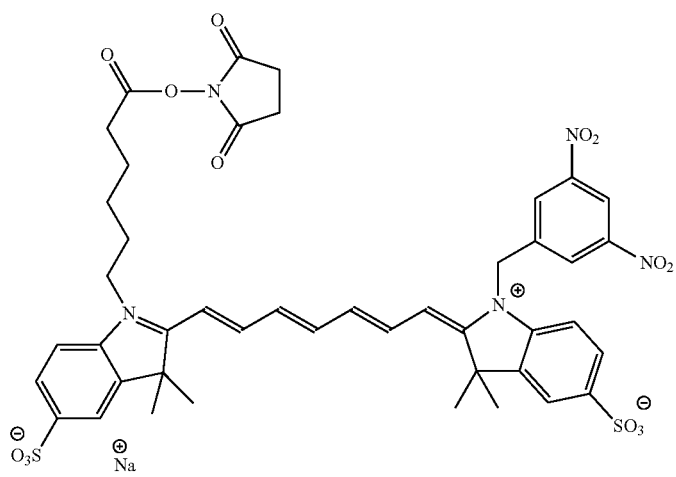
Cy7-Q

In one embodiment, the quencher dye is one of the following:

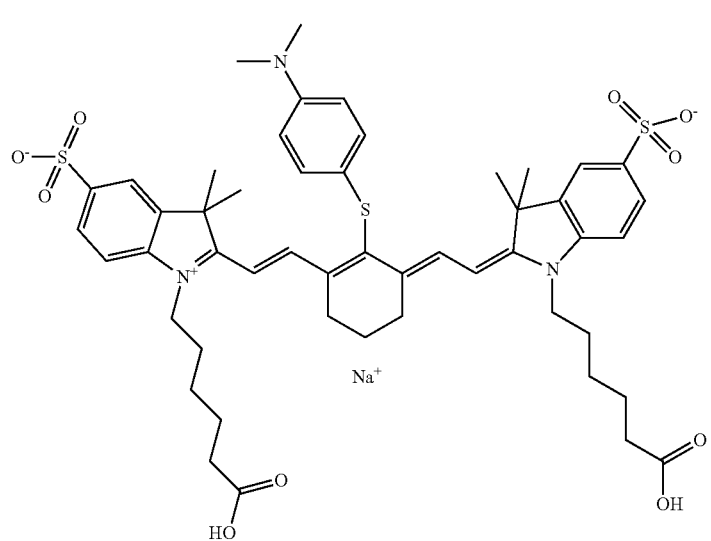

NIR Quencher I

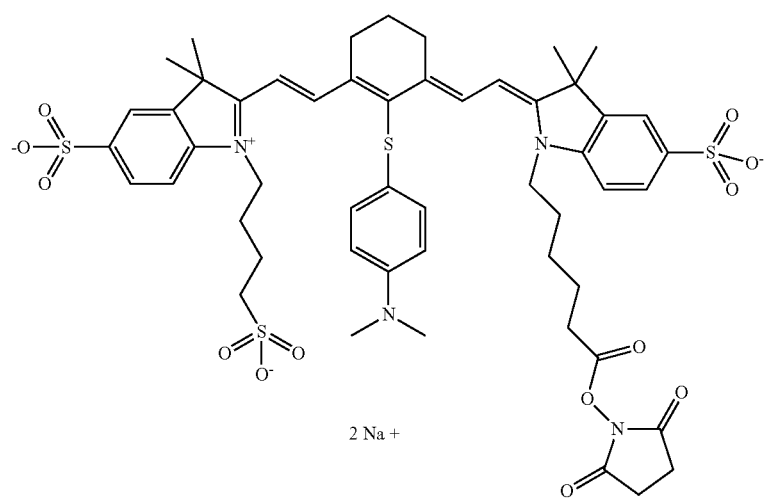

NIR Quencher II

In one embodiment, the quencher dye of the imaging probe of the present invention can be attached via an enzyme-specific cleavable spacer to the nanoparticle. In one embodiment the fluorescent dye of the imaging probe of the present invention can be attached via an enzyme-specific cleavable spacer to the nanoparticle. The cleavable spacer can comprise any biocompatible polymer.

Various cleavable spacers are contemplated for inclusion in the activatable probe of the present invention. The cleavable spacer may be naturally occurring or synthetic. Dyes may be attached to the cleavable spacer at any point, including at either end or along the linear or nonlinear chain.

Cleavable spacers may comprise a material made of two or more covalently linked monomer units in a linear or nonlinear fashion. This includes dimers, trimers, and higher oligomers, as well as copolymers, block copolymers, and crosslinked polymers. Examples of some useful polymers with the present invention include polylysine, poly-L-lysine, poly-D-lysine, polyarginine, polyornitine, polyglutamic acid, polypeptides comprising of L and/or D amino acids, as well as those comprised of unnatural amino acids, polyvinyl alcohol, polyacrylic acid, polymethacrylate, polyacrylamide, polyalkylcyanoacrylate, polyhydroxyacrylate, polysuccinimide, polysuccinic anhydride, poly(hydroxyethyl methacrylate) (HEMA), HPMA, polysaccharides, polyesters (e.g., polylactic acid, polylactides, polyhydroxybutanoates), dextran, aminodextran, modified dextrans, amdex®, oligonucleotides, chitosan, polyurethanes, polycarbonates, polystyrene, polyvinyl alcohol, polyacrylamides, chitosan, trimethyl chitosan, and derivatized chitosan. It also includes polymers that have been modified with additional functionalities in the side chain or the backbone to impart desired physicochemical properties and/or sites for covalent attachment to other molecules such as polystyrene, polystyrene-maleic anhydride, polyesters, polycarbonates, polylactides, polyurethanes, polyethelene, polydivinylbenzene, chitosan-cysteine, chitosan-thioglycolic acid, chitosan-4-thiobutylamidine, polycarbophilcysteamine, and polycarbophil-cysteine. Additional polymers include dendrimers (also called a cascade molecule, a polymer in which the atoms are arranged in multiple branches and/or sub-branches along a central backbone of carbon atoms). The examples given here are only illustrative and by no means limit or exclude this patent from the use of other polymers.

Polymers that may be used with the present invention also include or may comprise a nucleic acid, particularly in embodiments where the enzyme of interest will cleave the backbone sequence in one or more places. The nucleic acid may comprise DNA, RNA, singled-stranded, double-stranded, or more highly aggregated hybridization motifs, and any chemical modification thereof. Modifications include, but are not limited to, those providing chemical groups that incorporate additional charge, polarizability, hydrogen boding, electrostatic interaction, and fluxionality to the nucleic acid ligand bases or to the nucleic acid ligand as a whole. The nucleic acid may have modified internucleotide linkages to alter, for example, hybridization strength and resistance to specific and non-specific degradation. Modified linkages are well-known in the art and include, but are not limited to, methylphosphonates, phosphothioates, phosphodithionates, phospoamidites, and phosphodiester linkages. Alternatively, dephospho-linkages, also well-known in the art, can be introduced as bridges. These include, but are not limited to, siloxane, carbonate, carboxymethylester, acetamide, carbamate, and thioether bridges.

Polymers that may be used with the present invention also include or may comprise amino acids. amino acids include naturally occurring or synthetic amino acid in a L or D configuration, optionally comprising additional substituents in the alpha position or side chains. Amino acids with unnatural side chains are also specifically contemplated, as are amino acids in which additional methylene units have been introduced into the backbone, such as beta, gamma, delta, etc. In certain embodiments, the amino acids may be cyclic amino acids in which additional methylene units have been introduced on the backbone or side chains. The use of other amino acid mimics included in this definition is also contemplated and would be recognized by one of skill in the art.

Polymers that may be used with the present invention also include or may comprise peptides. Peptides comprise a synthetic or naturally occurring polymer of amino acids. Peptides include peptidomimetics, in which either natural or synthetic amino acids are linked by either amide bonds or non-amide bonds (such as peptoids, etc).

In one embodiment, the cleavable spacer may comprise a peptide, oligopeptide, polypeptide, protein, polysaccharide, nucleic acid, nucleotide, oligonucleotide, DNA, RNA, psuedopeptide, peptidomimetic, lipid, phospholipids, lipoprotein, lipopolysaccharide, or a synthetic polymer. Polypeptides useful as a cleavable spacer include, for example, polylysine, albumins, and antibodies. The cleavable spacer also can be a synthetic polymer such as polyglycolic acid, polylactic acid, poly(glycolic-colactic) acid, polydioxanone, polyvalerolactone, poly-ε-caprolactone, poly(3-hydroxybutyrate, poly(3-hydroxyvalerate)polytartronic acid, and poly(β-malonic acid). Cleavable spacers are known to the art and such cleavable spacers are described by way of example in U.S. Patent Publications Nos. 2006/0275775, US 2005/0014160, US 2005/0181989, US 2004/0137479, and WO 2004/026344.

In one embodiment, enzyme specificity is imparted through the use of enzyme cleavage-specific sequences, which can be varied depending upon the desired enzyme to be visualized. In another embodiment, enzyme specificity is imparted through the use of enzyme cleavage-specific peptide sequences, which can be varied depending upon the desired protease to be visualized. Moreover, other enzymatic pathways are amenable to this activation scheme. This approach has several major advantages over simple targeting: (1) a single enzyme molecule can cleave multiple dyes, resulting in signal amplification; (2) reduction of background signal of several orders of magnitude is possible because the quenched probe is optically silent until it is activated by its target; and (3) very specific enzyme activities can be potentially interrogated. All of these examples can lead to better imaging visualization of tumors and other disease states based on their enzyme over-expression profile because in most cancer and disease cells, the levels of certain proteases are highly elevated.

Many tumors have been shown to have elevated levels of proteolytic enzymes (protease) in adaptation to rapid cell cycling and for secretion to sustain invasion, metastasis formation, and angiogenesis. Because they are present at high levels in tumors and are elevated at an early stage, and their type and level are tightly associated with specific cells or physiological or pathological processes, proteases represent an attractive target for anti-tumor imaging and therapeutic strategies. Also they are much richer than DNA and mRNA in their concentrations.

An aspect of the present invention relates to a method of in vivo or in vitro photodetection or imaging comprising administering an imaging probe of the present invention to a subject, allowing a period of time to pass sufficient to allow for enzymatic activation of the imaging probe, and detecting the fluorescence of the dyes. The subject may be a mammal, such as a human. The method may comprise a method for screening a putative protease inhibitor. In certain embodiments, the method comprises a method of diagnosing or treating a disease. The disease may be a cell proliferative disease. The cell proliferative disease may be any type of cancer, such as breast cancer. In various embodiments, the disease may be an inflammatory disease, rheumatoid arthritis, a circulatory disease, atherosclerosis, a digestive disorder, ulcers, colon polyps, or is characterized by an activation of a proteolytic enzyme.

Fluorescence activation of the probe requires substrate access by the enzyme of interest. For example, in probes made by directly attaching a dye to the cleavable spacer, fluorescence activation involves access and cleavage of the cleavable spacer by the enzyme.

Fluorescence activation may caused by cleavage of a bond in the probe by an enzyme such as, for example, trypsin, a cathepsin, cathepsin D, cathepsin B, cathepsin H, cathepsin L, cathepsin S, urokinase, thrombin, plasmin, a plasminogen activator, a prostate specific antigen, a matrix metalloproteinase (MMP), a kallikrein, a human kallikrein, or human kallikrein 3, a caspase, a caspase 3, a caspase 8, a granzyme B, a calpain, etc. Specific enzyme cleavable linkers (e.g., moieties and/or amino acid sequences) that may be cleaved by these enzymes are known in the art (e.g., Asp-Val-Glu-Asp- to target caspase 3 [J. Liu et al. Bioorg Med Chem Lett 1999, 9, 3231-3236], Ile-Glu-Thr-Asp- to target caspase 8, Ala-Ala-Asp- to target granzyme B [J Biol Chem 2001, 276, 6974] Leu-Met- to target calpain [B. G. Rosser et al. Biol Chem 1993, 268, 23593]) and are specifically contemplated for inclusion in nanoparticles of the present invention. In certain embodiments, a nanoparticle comprises a cathepsin D cleavable linker (e.g., Gly-Pro-Ile-Cys(Et)-Phe-Phe-Arg-Leu-Gly).

Table 2 below provides additional examples of enzyme-cleavable linkers that may be included in imaging probes according to the present invention.

TABLE 2

| Sequence | Target | References: |
|---|---|---|
| Pro-Leu-Gly/Leu-Trp-Ala-D-Arg-NH2 | MMP-1 | Stack M.S. et al. J. Biol. Chem. 264, 4277-4281 |
| Pro-Cha-Abu/Smc-His-Ala-D-Arg-NH2 (Cha: cyclohexylalnine, Abu: alpha-aminobutyric acid Smc: S-methylcysteine) | MMP-1 | McGeehan G. M. et al. J. Biol. Chem. 269, 32814-32820 |
| Lys-Pro-Leu-Ala/Nva-Asp-Ala-Arg-NH2 | MMP-2 | |
| Pro-Leu-Gly/Leu-Ala-Arg-NH2 | MMP-2 | Knight C. G., FEBS 296, 3, 263-266 |
| Arg-Pro-Lys-Pro-Tyr-Ala/Nva-Trp-Met-Lys-NH2 | MMP-3 | Nagase H. et al. J. of Biol. Chemistry 1994, 269(33) 20952-20957 |
| Arg-Pro-Lys-Pro-Val-Glu/Nva-Trp-Arg-Lys-NH2 | MMP-3 | Nagase H. et al. J. of Biol. Chemistry 1994, 269(33) 20952-20957 |
| Arg-Pro-Leu-Ala/Leu-Trp-Arg-Ser(AHX)Cys (where AHX stands for aminohexanoic acid) | MMP-7 | McIntyre JO, Biochem J. 2004 Feb. 1; 377(Pt 3): 617-28. |
| Arg-Pro-Leu-Ala/Leu-Trp-Arg-Ser | MMP-7 | Welch A. R. et al. 1995, Arch. Biochem. Biophys. 324, 59 |
| Pro-Leu-Gly-Leu-Dpa-Ala-Arg-NH2 | MMP-7 | (Knight C. G., FEBS 296, 3, 263-266) |
| Ser-Gly-Lys-Gly-Pro-Arg-Gln/Ile-Thr-Ala | MMP-9 | Kridel S. J, J. of Biol Chem 2001, Vol 276, 23(8), 20572-20578 |
| Ser-Gly-Lys-Ile-Pro-Arg-Arg/Leu-Thr-Ala | MMP-9 | Kridel S. J, J. of Biol Chem 2001, Vol 276, 23(8), 20572-20578 |
| Pro-Gln-Gly-Ile-Ala | MMP-9 | Williams H. R et al. Int. J. Biochem. 1984 (16) 1321-1329 |
| Pro-Cha-Gly/Nva-His-Ala-NH2 (Nva: L-norvaline) | MMP-13 | Knäuper V. et al., J. of Biol. Chem. 1996, Vol 271, (3) 1544-1550 |
| Pro-Leu-Gly/Leu-Ala-Arg-NH2 | MMP-13 | Knäuper V. et al., J. of Biol. Chem. 1996, Vol 271, (3) 1544-1550 |
| Gly-Pro-Leu-Gly-Meth-Arg-Gly-Leu-NH2 | MMP13 | Deng S. J et al. J. of Biol. Chem. 2000, Vol. 275, No 40, 31422-31427 |
| PGSGR/SAG PGSGR/SASGTTGTG | uPA | Coombs G. S et al (1998) |
| SGR/SA GSGK/S | uPA | Ke S. H et al. (1997) |

TABLE 2-continued

| Sequence | Target | References: |
|---|---|---|
| D-Phe-Pip-Arg-pNA<br>D-Phe-Pro-Arg-pNA | Thrombin | Rijkers D. T. S. et al. (1995) |
| Ac-Nle-Thr-Pro-Arg-AMC | Thrombin | Backes B J et al. (2000) |
| Ac-Val-Thr-Pro-Arg-AMC | Thrombin | Harris J L et al. (2000) |
| Gly-Ser-Pro-Ala-Phe-Leu-Ala-Lys-D-Arg-Lys-Pro-Leu-Gly-Leu-Dap-Ala-Arg | Cathepsin E, MMPs, Cathepsin D and E, ADAM10 and ADAM17/TACE | |
| Lys-Pro-Leu-Gly-Leu-A2pr-Ala-Arg- | Matrix Metalloproteinases, and ADAM17/ Tumor Necrosis Factor Converting Enzyme (TACE) | |
| Pro-Cha-Gly-Nva-His-Ala-Dap | MMPs | |
| Ser-Glu-Val-Asn-Leu-Asp-Ala-Glu-Phe-Arg-Lys-Arg-Arg | β-Cleavage Site of Swedish-Type Amyloid Precursor Protein | |
| Gly-Gly-Val-Val-Ile-Ala-Thr-Val-Lys-D-Arg-D-Arg-D-Arg | gamma-secretase | |
| Gly-Lys-Pro-Ile-Leu-Phe-Phe-Arg-Leu-Lys-D-Arg | Cathepsin D and E | |
| Asp-Glu-Val-Asp-Ala-Pro-Lys- | Caspase-3 | |
| Ala-Pro-Ala-Lys-Phe-Phe-Arg-Leu-Lys | Proteinase A/Pepsin | |
| Tyr-Val-Ala-Asp-Ala-Pro-Lys- | Caspase-1 | |
| Pro-Cha-Gly-Cys(Me)-His-Ala-Lys | Collagenase | |
| Leu-Ala-Gln-Ala-Val-Arg-Ser-Ser-Ser-Arg-Dap- | ADAM17/TNF-α Converting Enzyme | |
| Gly-Phe-Ser-Pro-Tyr(NO2) | ACE2 | |

Matrix Metalloproteinases (MMPs) are among the most over-expressed proteases in cancers. They are one of the most attractive diagnostic markers, since their overexpression is tightly associated with the aggressive growth of the cancer cells. Thus, their detection can serve as a surrogate marker for tumor staging, metastasis and recurrence. They can also be used to examine the effectiveness of therapeutic inhibitors. Specifically MMP-2 and MMP-9 are attractive imaging targets due to their critical roles in angiogenesis and metastasis. Elevated levels of MMP-2 and MMP-9 have been correlated with increased aggressiveness of tumor cells. MMP-2 has been observed to be overexpressed in more aggressive tumor cell.

Thus, spacer groups containing peptide sequences recognized by MMP-2 can be used to produce a near infrared probe that undergoes fluorescence activation specifically in tumor tissues. The effectiveness of the activation by MMP-2 was examined by using HT1080 cancer cells as model cancer cells, shown in FIG. 4. Peptide sequence used as spacer groups and recognized by MMP-2 of the present invention include oligopeptides such as those disclosed in International Publication No. WO2004/026344.

Various other enzymes can be exploited to provide fluorescence activation in particular target tissues or samples and in particular diseases as disclosed in the prior art and in a publication by Mahmood et al. (Mahmood, U. and Weissleder, R. Molecular Cancer Therapeutics 2003, 2, 489-496).

The dye compounds, donor or acceptor, may be attached to the cleavable spacer by conjugation. Dyes may be conjugated to the cleavable spacer by the process of chemically associating or a chemical association between two or more chemical moieties; conjugation may directly associate two moieties, or conjugation may associate two moieties through one or more additional moiety. Conjugation can be achieved by the generation of a covalent bond. For example, a cleavable spacer may be conjugated to a dye via direct covalent bonding.

Attachment of dyes to the cleavable spacer can be accomplished through covalent bonds which can be made under mild reaction conditions. Classes of reactions for conjugating one or more moiety to a cleavable spacer include those which proceed under relatively mild conditions. These include, but are not limited to nucleophilic substitutions (e.g., reactions of amines, hydrazines, hydrazides, thiols and alcohols with acyl halides, active esters, carbonyls, and carbon-halide bonds), electrophilic substitutions (e.g., enamine reactions) and additions to carbon-carbon and carbonheteroatom multiple bonds (e.g., Michael reaction, Diels-Alder addition).

Several approaches are available for conjugating a cleavable spacer to a dye. In certain embodiments, specific peptide sequences may be used as enzyme cleavable linkers for this purpose, and peptide sequences possess the advantage of being easily assembled on the solid-phase by the Fmoc or Boc strategy. The dye units can easily be installed on the peptide via terminal or side chain $NH_2$ functions (using activated esters of a dye, Michael additions, etc.), as well as OH, SH, and carboxylic functions. In certain embodiments, terminal or lysine side chains $NH_2$ functions or ornitine $NH_2$ functions of a peptide cleavable spacer are reacted in combination with an activated ester of a dye.

It is also possible to use modified or unnatural amino acids to conjugate a peptide (e.g., a cleavable spacer) to a dye involving various functional groups and chemical reactions. See U.S. Patent Publication No. 20090209508. For example, the dye can be attached to the peptide on the solid-phase. Similarly, other enzyme cleavable spacers can be employed including saccharides, polysaccharides, polyesters, and oligonucleotides to target a known over expressed enzyme which is associated with a targeted pathology.

Oligonucleotide linkers (serving as cleavable spacers) may be synthesized by a number of different approaches including commonly known methods of solid-phase chemistry. Oligonucleotide linkers bearing a photosensitizer in one end and a spacer with the appropriate functional group at the opposite end can be synthesized on an automated DNA synthesizer (e.g. P.E. Biosystems Inc. [Foster Clif, Calif.] model 392 or 394) or using standard chemistry, such as phosphoramidite chemistry (Agrawal and Zamecnik, Nucleic Acids Res., 18(18):5419-5423: 1990). When using automated DNA synthesizers, the dye and spacers have the advantage of being introduced during automated synthesis. Alternatively, one or more of these moieties can be introduced either before or after automated synthesis. Additional strategies for conjugation to growing or complete sequences will be apparent to those skilled in the art. Following automated synthesis the reaction products may be cleaved from their support, protecting groups removed and the linker-dye be purified by methods known in the art, e.g. chromatography, extraction, gel filtration, or high pressure liquid chromatography (HPLC).

The enzyme-cleavable linker can be attached to the conjugate chemoselectively. For this purpose, a chemoselective functional group pair should be utilized. Chemoselective functional groups include, but are not limited to, amine-activated ester, hydrazine derivatives-activated ester, hydrazine derivatives-carbonyl, thiols-substitution reactions (carbon-halide bonds, alkylsulphonic esters), thiols-Michael additions (maleiimides, acrylates, vinylsulphones, vinylketones, etc) thiols-thioligation or natural chemical ligation (requires either an N-terminal cysteine with a thioester, or 1-hydroxy-8-sulfenyl dibenzofuran moiety with a thiol, or aminoethane sulphonyl azides with thio acids, etc.), thiol-disulfide bonds, amines-substitution reactions (activated carbon-halide bonds, activated esters, and activated alkylsulphonic esters), amines-Michael additions (maleiimides, acrylates, vinylsulphones, vinylketones, etc), diels-alder reactions (requiring a diene and a dienophile), 1,3-dipolar additions, etc. The proper choice of chemoselective reaction will be obvious to one skilled in the art (U.S. Patent Publication No. 20090209508).

Optimal fluorescence quenching may be obtained by varying the ratio of donor dyes to acceptor dyes. The ratio of donor dyes to acceptor dyes ranges may vary from about (i) 1:1 to about 1000:1, (ii) 1:1 to about 100:1, (iii) 1:1 to about 10:1, (iv) 1:1 to about 5:1, (v) 1:1 to about 1000:1, (vi) 1:1 to about 100:1, (vii) 1:1 to about 10:1 or (viii) 1:1 to about 5:1. Alternatively, the ratio of acceptor dye to donor dye may vary from about (i) 1:1 to about 1000:1, (ii) 1:1 to about 100:1, (iii) 1:1 to about 10:1, (iv) 1:1 to about 5:1, (v) 1:1 to about 1000:1, (vi) 1:1 to about 100:1, (vii) 1:1 to about 10:1 or (viii) 1:1 to about 5:1.

Other diagnostic agents (beside the dyes disclosed above), such as therapeutic or targeting agents, can also be attached to the imaging probe of the present invention via enzyme-specific spacer groups and can be released from the imaging probe for imaging and therapeutic application.

The present nanoparticles can also be useful as a carrier for carrying a biological, pharmaceutical or diagnostic component. Specifically, the nanoparticle used as a carrier does not necessarily encapsulate a specific therapeutic or an imaging component, but rather serves as a carrier for the biological, pharmaceutical or diagnostic components. Biological, pharmaceutical or diagnostic components such as therapeutic agents, diagnostic agents, dyes or radiographic contrast agents. The term "diagnostic agent" includes components that can act as contrast agents and thereby produce a detectable indicating signal in the host mammal. The detectable indicating signal may be gamma-emitting, radioactive, echogenic, fluoroscopic or physiological signals, or the like. The term biomedical agent, as used herein, includes biologically active substances which are effective in the treatment of a physiological disorder, pharmaceuticals, enzymes, hormones, steroids, recombinant products, and the like. Exemplary therapeutic agents are antibiotics, thrombolytic enzymes such as urokinase or streptokinase, insulin, growth hormone, chemotherapeutics such as adriamycin and antiviral agents such as interferon and acyclovir. Upon enzymatic degradation, such as by a protease or a hydrolase, therapeutic agents can be released over a period of time. A variety of drugs with diverse characteristics, including genes and proteins, can also be incorporated into the imaging probe of the present invention and released upon activation.

Included within the scope of the invention are compositions comprising the fluorescent activatable probes of the current invention and a suitable targeting molecule. As used herein, the term "targeting molecule" refers to any molecule, atom, or ion linked to the polymer shell of the nanoparticle of the current invention that enhances binding, transport, accumulation, residence time, bioavailability or modifies biological activity of the polymer networks or biologically active compositions of the current invention in the body or cell. The targeting molecule will frequently comprise an antibody, fragment of antibody or chimeric antibody molecules typically with specificity for a certain cell surface antigen. It could also be, for instance, a hormone having a specific interaction with a cell surface receptor, or a drug having a cell surface receptor. For example, glycolipids could serve to target a polysaccharide receptor. It could also be, for instance, enzymes, lectins, and polysaccharides. Low molecular mass ligands, such as folic acid and derivatives thereof are also useful in the context of the current invention. The targeting molecules can also be polynucleotide, polypeptide, peptidomimetic, carbohydrates including polysaccharides, derivatives thereof or other chemical entities obtained by means of combinatorial chemistry and biology. Targeting molecules can be used to facilitate intracellular transport of the nanoparticles of the invention, for instance transport to the nucleus, by using, for example, fusogenic peptides as targeting molecules described by Soukchareun et al., Bioconjugate Chem., 6, 43, (1995) or Arar et al., Bioconjugate Chem., 6, 43 (1995), caryotypic peptides, or other biospecific groups providing site-directed transport into a cell (in particular, exit from endosomal compartments into cytoplasm, or delivery to the nucleus).

The described composition can further comprise a biological, pharmaceutical or diagnostic component that includes a targeting moiety that recognizes the specific target cell. Recognition and binding of a cell surface receptor through a targeting moiety associated with a described nanoparticle used as a carrier can be a feature of the described compositions. For purposes of the present invention, a compound carried by the nanoparticle may be referred to as a "carried" compound. For example, the biological, pharmaceutical or diagnostic component that includes a targeting moiety that recognizes the specific target cell described above is a "carried" compound. This feature takes advantage of the understanding that a cell surface binding event is often the initiating step in a cellular cascade leading to a range of events, notably receptor-mediated endocytosis. The term "receptor mediated endocytosis" ("RME") generally describes a mechanism by which, catalyzed by the binding of a ligand to a receptor disposed on the surface of a cell, a receptor-bound ligand is internalized within a cell. Many proteins and other structures enter cells via receptor mediated endocytosis, including insulin, epidermal growth factor, growth hormone, thyroid stimulating hormone, nerve growth factor, calcitonin, glucagon and many others.

Receptor Mediated Endocytosis affords a convenient mechanism for transporting a described nanoparticle, possibly containing other biological, pharmaceutical or diagnostic components, to the interior of a cell. In receptor mediated endocytosis (RME), the binding of a ligand by a receptor disposed on the surface of a cell can initiate an intracellular signal, which can include an endocytosis response. Thus, a nanoparticle used as a carrier with an associated targeting moiety, can bind on the surface of a cell and subsequently be invaginated and internalized within the cell. A representative, but non-limiting, list of moieties that can be employed as targeting agents useful with the present compositions includes proteins, peptides, aptomers, small organic molecules, toxins, diptheria toxin, pseudomonas toxin, cholera toxin, ricin, concanavalin A, Rous sarcoma virus, Semliki forest virus, vesicular stomatitis virus, adenovirus, transferrin, low density lipoprotein, transcobalamin, yolk proteins, epidermal growth factor, growth hormone, thyroid stimulating hormone, nerve growth factor, calcitonin, glucagon, prolactin, luteinizing hormone, thyroid hormone, platelet derived growth factor, interferon, catecholamines, peptidomimetrics, glycolipids, glycoproteins and polysaccharides. Homologs or fragments of the presented moieties can also be employed. These targeting moieties can be associated with a nanoparticle and be used to direct the nanoparticle to a target cell, where it can subsequently be internalized. There is no requirement that the entire moiety be used as a targeting moiety. Smaller fragments of these moieties known to interact with a specific receptor or other structure can also be used as a targeting moiety.

An antibody or an antibody fragment represents one class of biotargeting moieties that can be utilized to enhance the uptake of nanoparticles into a cell. Antibodies may be prepared by any of a variety of techniques known to those of ordinary skill in the art. Antibodies can be produced by cell culture techniques, including the generation of monoclonal antibodies or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). A superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, (Eur. J. Immunol. 1976, 6511-519), and improvements thereto.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

A number of "humanized" antibody molecules comprising an antigen-binding site derived from a non-human immunoglobulin have been described (Winter et al. Nature 1991, 349, 293-299; Lobuglio et al. Proc. Nat. Acad. Sci. USA 1989, 86, 4220-4224). These "humanized" molecules are designed to minimize unwanted immunological response toward rodent antihuman antibody molecules that limits the duration and effectiveness of therapeutic applications of those moieties in human recipients.

Affibody® affinity ligands are research reagents, produced using protein-engineering technologies. They are small, simple proteins composed of a three-helix bundle based on the scaffold of one of the IgG-binding domains of Protein A. Protein A is a surface protein from the bacterium *Staphylococcus aureus*. This scaffold has excellent features as an affinity ligand and can be designed to bind with high affinity to any given target protein. The domain consists of 58 amino acids, 13 of which are randomized to generate Affibody® libraries with a large number of ligand variants. Thus, the libraries consist of a multitude of protein ligands with an identical backbone and variable surface-binding properties. In function, Affibody® Molecules mimic monoclonal antibodies. Compared to antibodies, the most striking dissimilarity of Affibody® Molecules is the small size. Affibody® Molecules have a molecular weight of 6 kDa, compared to the molecular weight of antibodies, which is 150 kDa. In spite of its small size, the binding site of Affibody® Molecules is similar to that of an antibody. The advantages of Affibody® Molecules over antibodies include their small size, the simple structure of the molecules, their robust physical properties able to withstand a broad range of analytical conditions including extreme pH and elevated temperature, and their ability to fold correctly intracellularly. Conjugation or directed coupling to nanolatex particles for use in accordance with the present invention is facilitated by the C-terminal cysteine. Affibody® Molecules have highly competitive properties for applications within affinity purification, sample preparation and protein detection.

Vitamins and other essential minerals and nutrients can be utilized as targeting moiety to enhance the uptake of nanoparticles by a cell. In particular, a vitamin ligand can be selected from the group consisting of folate, folate receptor-binding analogs of folate, and other folate receptor-binding ligands, biotin, biotin receptor-binding analogs of biotin and other biotin receptor-binding ligands, riboflavin, riboflavin receptor-binding analogs of riboflavin and other riboflavin receptor-binding ligands, and thiamin, thiamin receptor-binding analogs of thiamin and other thiamin receptor-binding ligands. Additional nutrients believed to trigger receptor mediated endocytosis, and thus also having application in accordance with the presently disclosed method, are carnitine, inositol, lipoic acid, niacin, pantothenic acid, pyridoxal, and ascorbic acid, and the lipid soluble vitamins A, D, E and K. Furthermore, any of the "immunoliposomes" (liposomes having an antibody linked to the surface of the liposome) described in the prior art are suitable for use with the described compositions.

Since not all natural cell membranes possess biologically active biotin or folate receptors, use of the described compositions in vitro on a particular cell line can involve altering or otherwise modifying that cell line first to ensure the presence of biologically active biotin or folate receptors. Thus, the number of biotin or folate receptors on a cell membrane can be increased by growing a cell line on biotin or folate deficient substrates to promote biotin and folate receptor production, or by expression of an inserted foreign gene for the protein or apoprotein corresponding to the biotin or folate receptor.

Receptor mediated endocytosis (RME) is not the exclusive method by which the described nanoparticle can be translocated into a cell. Other methods of uptake that can be exploited by attaching the appropriate entity to a nanoparticle include the advantageous use of membrane pores. Phagocytotic and pinocytotic mechanisms also offer advantageous mechanisms by which a nanoparticle can be internalized inside a cell.

The recognition moiety can further comprise a sequence that is subject to enzymatic or electrochemical cleavage. The recognition moiety can thus comprise a sequence that is susceptible to cleavage by enzymes present at various locations inside a cell, such as proteases or restriction endonucleases (e.g. DNAse or RNAse).

A cell surface recognition sequence is not a requirement. Thus, although a cell surface receptor targeting moiety can be useful for targeting a given cell type, or for inducing the association of a described nanoparticle with a cell surface, there is no requirement that a cell surface receptor targeting moiety be present on the surface of a nanoparticle.

To assemble the biological or pharmaceutical components to a described fluorescent activatable probe used as a carrier, the components can be associated with the nanolatex particle carrier through a linkage. By "associated with", it is meant that the component is carried by the fluorescent activatable probe. The component can be dissolved and incorporated in the fluorescent activatable probe non-covalently.

Generally, any manner of forming a linkage between a biological or pharmaceutical component of interest and a fluorescent activatable probe used as a carrier can be utilized. This can include covalent, ionic, or hydrogen bonding of the targeting moiety to the exogenous molecule, either directly or indirectly via a linking group. The linkage is typically formed by covalent bonding of the biological or pharmaceutical component to the fluorescent activatable probe used as a carrier through the formation of amide, ester or imino bonds between acid, aldehyde, hydroxy, amino, or hydrazo groups on the respective components of the complex. Art-recognized biologically labile covalent linkages such as imino bonds and so-called "active" esters having the linkage —COOCH, —O—O— or —COOCH are preferred. The biological or pharmaceutical component of interest may be attached to the pre-formed fluorescent activatable probe or alternately the component of interest may be pre-attached to a polymerizeable unit and polymerized directly into the fluorescent activatable probe during the nanolatex particle preparation. Hydrogen bonding, e.g., that occurring between complementary strands of nucleic acids, can also be used for linkage formation.

After a sufficiently pure nanoparticle, optionally comprising a nanoparticle with a biological, pharmaceutical or diagnostic component, has been prepared, it might be desirable to prepare the nanoparticle in a pharmaceutical composition that can be administered to a subject or sample. Administration techniques include parenteral administration, intravenous administration and infusion directly into any desired target tissue, including but not limited to a solid tumor or other neoplastic tissue. Purification can be achieved by employing a final purification step, which dissolves the nanoparticle in a medium comprising a suitable pharmaceutical composition. Suitable pharmaceutical compositions generally comprise an amount of the desired nanoparticle with active agent in accordance with the dosage information (which is determined on a case-by-case basis). The described nanoparticles are admixed with an acceptable pharmaceutical diluent or excipient, such as a sterile aqueous solution, to give an appropriate final concentration. Such formulations can typically include buffers such as phosphate buffered saline (PBS), or additional additives such as pharmaceutical excipients, stabilizing agents such as BSA or HSA, or salts such as sodium chloride.

For parenteral administration it is generally desirable to further render such compositions pharmaceutically acceptable by insuring their sterility, non-immunogenicity and non-pyrogenicity. Such techniques are generally well known in the art. Moreover, for human administration, preparations should meet sterility, pyrogenicity, general safety and purity standards as required by FDA Office of Biological Standards. When the described nanoparticle composition is being introduced into cells suspended in a cell culture, it is sufficient to incubate the cells together with the nanoparticle in an appropriate growth media, for example Luria broth (LB) or a suitable cell culture medium. Although other introduction methods are possible, these introduction treatments are preferable and can be performed without regard for the entities present on the surface of a nanoparticle used as a carrier.

Included within the scope of the invention are compositions comprising nanoparticles of the current invention and other suitable imagable moieties. The nature of the imagable moiety depends on the imaging modality utilized in the diagnosis. The imagable moiety should be capable of detection either directly or indirectly in an in vivo diagnostic imaging procedure, for example, moieties which emit or may be caused to emit detectable radiation (e.g. by radioactive decay, fluorescence excitation, spin resonance excitation, etc.), moieties which affect local electromagnetic fields (e.g. paramagnetic, superparamagnetic, ferrimagnetic or ferromagnetic species), moieties which absorb or scatter radiation energy (e.g. chromophores, particles (including gas or liquid containing vesicles), heavy elements and compounds thereof, etc.), and moieties which generate a detectable substance (e.g. gas microbubble generators), etc.

A very wide range of materials detectable by diagnostic imaging modalities is known from the art. Thus, for example, for ultrasound imaging an echogenic material, or a material capable of generating an echogenic material will normally be selected, for X-ray imaging the imagable moieties will generally be or contain a heavy atom (e.g. of atomic weight 38 or above), for magnetic resonance imaging (MRI) the imagable moieties will either be a non zero nuclear spin isotope (such as 19 F) or a material having unpaired electron spins and hence paramagnetic, superparamagnetic, ferrimagnetic or ferromagnetic properties, for light imaging the imagable moieties will be a light scatterer (e.g. a colored or uncolored particle), a light absorber or a light emitter, for magnetometric imaging the imagable moieties will have detectable magnetic properties, for electrical impedance imaging the imagable moieties will affect electrical impedance and for scintigraphy, SPECT, PET etc. the imagable moieties will be a radionuclide.

Examples of the suitable imagable moieties are widely known from the diagnostic imaging literature, e.g. magnetic iron oxide particles, gas-containing vesicles, chelated paramagnetic metals (such as Gd, Dy, Mn, Fe, etc.). Imagable moieties include: chelated paramagnetic metal ions such as Gd, Dy, Fe, and Mn, especially when chelated by macrocyclic chelant groups (e.g. tetraazacyclododecane chelants such as 1,4,7,10-tetraazacyclododecane-N,N',N'',N'''-tetraacetic acid (DOTA), 1,4,7,10-tetraazacyclododecane-N,N',N''-triacetic acid (D03A), HP-D03A (10-(2-hydroxypropyl)-1,4,7, 10-tetraazacyclododecane-1,4,7 triacetic acid) and analogues thereof; or by linker chelant groups such as DTPA (N,N,N', N'',N''-diethylene-triaminepentaacetic acid (DTPA), DTPA-BMA (N,N,N',N'',N''-diethylenetriaminepentaacetic acid bismethylamide), DPDP (N,N'-dipyridoxylethylenediamine-N,N'-diacetate-5,5'-bis(phosphate), ethylenediamine-N,N, N',N'-tetraacetic acid (EDTA), 1-oxa-4,7,10-triazacyclododecane-N,N',N''-triacetic acid (OTTA), trans(1,2)-cyclohexanodiethylene-triamine-pentaacetic acid (CDTPA), etc; metal radionuclide such as 90 Y, 99m Tc, 111 In, 47 Sc, 67 Ga, 51 Cr, 177m Sn, 67 Cu, 167 Tm, 97 Ru, 188 Re, 177 Lu, 199 Au, 203 Pb and 141 Ce; superparamagnetic iron oxide crystals; chromophores and fluorophores having absorption and/or emission maxima in the range 300-1400 nm, especially 600 nm to 1200 nm, in particular 650 to 1000 nm; vesicles containing fluorinated gases (i.e. containing materials in the gas phase at 37° C. which are fluorine containing, eg. SF 6 or perfluorinated C 1-6 hydrocarbons or other gases and gas precursors listed in WO97/29783); chelated heavy metal cluster ions (e.g. W or Mo polyoxoanions or the sulphur or mixed oxygen/sulphur analogs); covalently bonded non-metal atoms which are either high atomic number (e.g. iodine) or are radioactive, e.g. 123 I, 131 I, etc. atoms; iodinated compound containing vesicles; etc.

Stated generally, the imagable moieties may be (1) a chelatable metal or polyatomic metal-containing ion (i.e. TcO, etc), where the metal is a high atomic number metal (e.g. atomic number greater than 37), a paramagnetic species (e.g. a transition metal or lanthanide), or a radioactive isotope, (2) a covalently bound non-metal species which is an unpaired electron site (e.g. an oxygen or carbon in a persistent free radical), a high atomic number non-metal, or a radioisotope, (3) a polyatomic cluster or crystal containing high atomic number atoms, displaying cooperative magnetic behavior (e.g. superparamagnetism, ferrimagnetism or ferromagnetism) or containing radionuclides, (4) a gas or a gas precursor (i.e. a material or mixture of materials which is gaseous at 37° C.), (5) a chromophore (by which term species which are fluorescent or phosphorescent are included), e.g. an inorganic or organic structure, particularly a complexed metal ion or an organic group having an extensive delocalized electron system, or (6) a structure or group having electrical impedance varying characteristics, e.g. by virtue of an extensive delocalized electron system. Examples of particular imagable moieties are described in US 2009/0098057, incorporated herein by reference.

In one embodiment, the fluorescent activatable probe of the present invention is administered as a pharmaceutical formulation comprising the nanoparticle in a form suitable for administration to a mammal. The administration is suitable for being carried out by injection or infusion of the formulation such as an aqueous solution. The formulation may contain one or more pharmaceutical acceptable additives and/or excipients e.g. buffers; solubilizers such as cyclodextrins; or surfactants such as Pluronic, Tween or phospholipids. Further, stabilizers or antioxidants such as ascorbic acid, gentisic acid or para-aminobenzoic acid and also bulking agents for lyophilisation such as sodium chloride or mannitol may be added.

In one embodiment, the present invention also provides a pharmaceutical composition comprising an effective amount (e.g. an amount effective for enhancing image contrast in an in vivo imaging procedure) of a composition of the nanoparticle-based contrast agent or dye of the present invention or a salt thereof, together with one or more pharmaceutically acceptable adjuvants, excipients or diluents.

A further aspect the invention provides the use of a composition of the fluorescent activatable probe of the present invention for the manufacture of a contrast medium for use in a method of diagnosis involving administration of said probe to a human or animal body and generation of an image of at least part of said body.

Still a further aspect of the invention provides a method of generating enhanced images of a human or animal body previously administered with the nanoparticle-based contrast agent composition which method comprises generating an image of at least part of said body.

The following examples illustrate but do not limit the scope of the invention.

SPECIFIC EXAMPLES

Example 1

Preparation of Amine-Terminated Polyethylene Glycol Methacrylate Hydrochloride

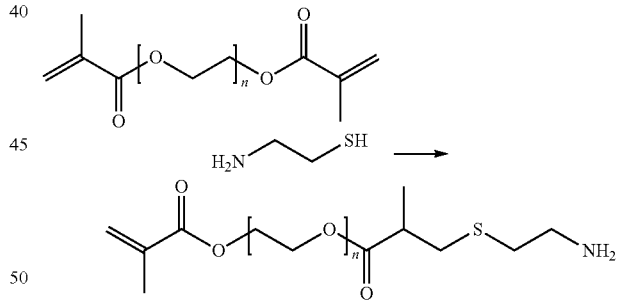

Polyethyleneglycol dimethacrylate (Aldrich, Mn=875, 335 g) was mixed with 100 ml of methanol and treated with cysteamine (Aldrich, 5.8 g) and diisopropylethylamine (Hunigs base) and was stirred at room temperature for 2 days and concentrated using a rotary evaporator. The residue was taken up in 1 L of ethyl acetate and extracted with aqueous 10% HCl. The aqueous layer was collected and made basic by the addition of 50% aqueous sodium hydroxide followed by extraction with ethyl acetate. The organic layer was dried over MgSO$_4$, filtered and concentrated. The residue was taken up. This material was washed with fresh diethyl ether, which was decanted. The residue was concentrated using a rotary evaporator to give 37 g of the desired product as the hydrochloride salt. The material was characterized by NMR spectroscopy, as follows: H-NMR (300 MHZ, CDCl$_3$): D 1.18 (d, 3H), 1.93

(bs, 3H), 2.04 (bs, 2H), 2.43-2.77 (bm, 7H), 3.6-3.7 (vbs, —CH$_2$CH$_2$O—), 3.73 (bt, 2H), 3.29 (bt, 2H), 5.56 (bs, 1H), 6.12 (bs, 1H).

Example 2

Preparation of Particle Comprised of Methoxyethyl Methacrylate (45% w/w), Divinylbenzene (4%), Ethylstyrene (1%), and Amine-Terminated Polyethylene Glycol Methacrylate Hydrochloride of Example 1 (50%)

A 500 ml 3-neck round bottomed flask was modified with Ace #15 glass threads at the bottom and a series of adapters allowing connection of 1/16 inch ID Teflon tubing. The flask (hereafter referred to as the "header" flask) was outfitted with a mechanical stirrer, rubber septum with syringe needle nitrogen inlet. The header contained methoxyethyl methacrylate (5.63 g), divinylbenzene (0.63 g, mixture of isomers, 80% pure with remainder being ethylstyrene isomers), amine-terminated polyethylene glycol ether methacrylate hydrochloride (6.25 g, M$_n$=940). A 1 L 3-neck round bottomed flask outfitted with a mechanical stirrer, reflux condenser, nitrogen inlet, and rubber septum (hereafter referred to as the "reactor") was charged with 2,2'-azobis(N,N'-dimethyleneisobutyramidine)dihydrochloride (0.06 g), cetylpyridinium chloride (0.31 g), sodium bicarbonate (0.06 g) and distilled water (78.38 g). The reactor contents were composed of distilled water (159.13 g), 2,2'-azobis(N,N'-dimethyleneisobutyramidine)dihydrochloride (0.06 g), sodium bicarbonate (0.06 g) and cetylpyridinium chloride (0.94 g). Both the header and reactor contents were stirred until homogeneous and were bubble degassed with nitrogen for 20 minutes. The reactor flask was placed in a thermostatted water bath at 60° C. and the header contents were added to the reactor over two hours using a model QG6 lab pump (Fluid Metering Inc. Syossett, N.Y.). The reaction mixture was then allowed to stir at 60° C. for 16 hours. The latex was treated twice with 100 cc Dowex 88 ion exchange resin and dialyzed for 48 hours using a 14K cutoff membrane to afford to afford 312 g of a clear latex of 3.26% solids. The volume average diameter was found to be 20.89 nm with a coefficient of variation of 0.24 by quasi-elastic light scattering.

Example 3

Preparation of Dye 4

This dye was prepared using 2,3,3-trimethyl-1-dodecyl-3H-Indolium perchlorate (4.28 g, 10 mmol) and the dianil (1.4 g, 5 mmol) in 40 mL of acetic anhydride containing triethylamine (1.5 g, 15 mmoles). The reaction time was 5 minutes. The reaction was cooled to 25° C. and poured into 2 liters of ice water with vigorous stirring. The water was decanted and the oil was dissolved in 100 mL of 80/20 dichlomethane-methanol. The material was chromatographed on a silica gel column eluting with 80/20 dichlomethane-methanol. Evaporation of the solvent after drying with anhydrous magnesium sulfate afforded pure dye (4 g, 32% yield), with absorption maximum 747 nm in methanol with extinction coefficient of 220,020.

Example 4

Preparation of Dye 2

This dye was prepared using 2,3,3-trimethyl-1-butyl-3H-Indolium perchlorate (12 g, 38 mmoles) and the dianil (5.4 g, 19 moles) in 100 mL of acetic anhydride containing tributylamine (10.5 g, 57 mmoles). The reaction was carried out for 15 minutes, cooled to 25° C. and poured into 2000 mL of ice water with vigorous stirring. The water was decanted from the oily product then chromatographed on silica gel eluting with 90/10 methylene chloride-methanol. Evaporation of the solvent after drying with anhydrous magnesium sulfate afforded pure dye (8 g, 71% yield), with absorption maximum 637 nm in methanol with extinction coefficient of 259,500.

Example 5

Loading of Particle with Dye 4

Under dim lighting, a dye stock solution of 0.0903% w/w was prepared by dissolving 0.0296 g of Dye 4 in sufficient tetrahydrofuran to afford a final solution weight of 29.8012 g. A 1.9627 g portion of the dye solution was added to a glass vial and was diluted to a final weight of 10.0 g with tetrahydrofuran. 10.0185 g of particle solution from Example 2 was added to the vial and the solution was stripped to approximately 40-50% volume on a rotary evaporator. Residual tetrahydrofuran was further removed by twice adding 3-5 ml distilled water and again stripping ~1/4 to 1/3 of the volatiles. 9.4467 g of a loaded particle (LP-4) of 3.45% solids containing $4.97 \times 10^{-3}$ mol dye per gram of solid latex.

Example 6

Loading of Particle with Dye 2

Under dim lighting, a dye stock solution (0.0402% w/w) was prepared by dissolving 0.0101 g of Dye 2 in sufficient tetrahydrofuran to afford a final solution weight of 25.1201 g. A 3.9146 g portion of the dye solution was added to a glass vial and was diluted to a final weight of 10.0 g with tetrahydrofuran. 10.0451 g of particle solution from Example 2 was added to the vial and the solution was stripped to approximately 40-50% volume on a rotary evaporator. Residual tetrahydrofuran was further removed by twice adding 3-5 ml distilled water and again stripping ~1/4 to 1/3 of the volatiles. 10.9030 g of a loaded particle (LP-2) of 3.56% solids containing $4.99 \times 10^{-3}$ mol dye per gram of solid latex.

Example 7

Preparation of Fluorescent Activatable Probes

MMP-2 peptide (NH2-GKGPLGVRGC-NH2) and the scrambled control peptide (NH2-GKGVRLGPGC-NH2) were ordered from NeoBioScience, Inc (Cambridge, Mass.). In order to attachment the NIR quencher dye to the peptide MMP-2 or control peptide (0.5 mg) and NIR quencher (1.5 mg) were added together and incubated in 500 μL of 0.1 M PBS/10 mM EDTA (pH 7.2) at room temperature for 1 h. The reaction mixture was used for the next step reaction without further purification. The conjugation of the peptide-quencher conjugate to nanoparticles was carried out by the following steps:

(1) Modification of nanoparticles with BMPS. Kodak X-sight 761 nanoparticles (Carestream; New Haven, Conn.), (118 μL, 173 μM) were added to 200 μL of 0.1 M PBS (pH 7.5) and then added with 30.6 μL of 100 mM BMPS dissolved in dry dimethyl sulfoxide (DMSO). The mixture was incubated at room temperature for 1 h. The maleimide-modified nanoparticles were purified on an illustra NAP-10 column eluted with 0.1 M PBS/10 mM EDTA (pH 7.2).

(2) Attachment of peptide-quencher to nanoparticles.

(3) The above Maleimide-modified nanoparticles and peptide-quencher were mixed together and incubated at room temperature for 2 h. The nanoparticle-peptide-quencher conjugates were then purified on a Biogel P30 column eluted with 0.1 M PBS (pH 7.2).

Example 8

MMP-2 Activatable Probes

Figure 2:
FIG. 2 shows one embodiment of the fluorescent activatable probes of the present invention, which are optically silent (quenched, no fluorescence) in their native (quenched) state.

Probes were constructed using the Kodak X-sight 761 nanoparticle (Carestream; New Haven, Conn.), NIR Quencher II, and an MMP-2 cleavable peptide or a scrambled peptide control. The same amount of each probe (X-sight 761, X-sight 761+quencher linked with MMP-2 cleavable peptide, and X-sight 761+quencher linked with a scrambled peptide) was added to a 96 well plate. The probes were imaged using an Image Station 4000MM. Quenching efficiency of >99% was achieved. FIG. 2 shows the fluorescence images.

TABLE 3

|  | Amount (pmol) | concentration (nM) | Net Intensity (arbitrary units) | Quenching Efficiency |
| --- | --- | --- | --- | --- |
| X-sight 761 | 50 | 500 | 41002712 |  |
| Activatable probe | 50 | 500 | 305814.47 | 0.99 |
| Scrambled probe | 50 | 500 | 190521.56 | 1 |

Example 9

Activation of MMP-2 Activatable Probes In Vitro

Figure 3:
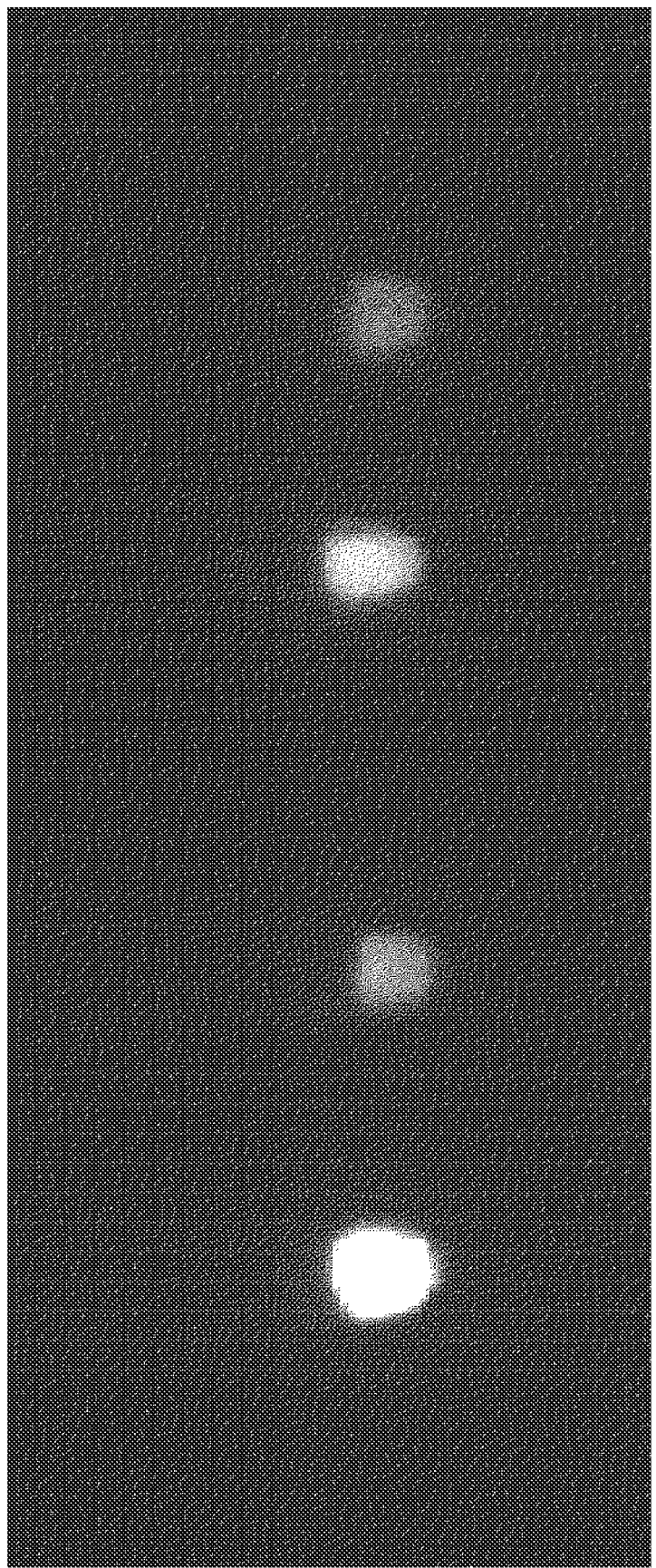
FIG. 3 shows the activation of a fluorescent activatable probe in the presence of an enzyme (MMP-2). Sample A shows activatable probes in the presence of the enzyme. Sample B shows activatable probes without enzyme present. Sample C shows the scrambled control probe in the presence of enzyme. Sample D shows the scrambled control probe without enzyme present.

The fluorescent activatable probes of Example 8 with and without MMP-2 enzyme were incubated at 37° C. for 2 hr. Then the image was taken on a Image Station 4000MM. FIG. 3 shows the fluorescence images.

TABLE 4

| Sample | Net Intensity (arbitrary units) | Fold Activation |
| --- | --- | --- |
| 1 | 1648693.13 | 4.7 |
| 2 | 347413.438 | 1.0 |
| 3 | 574253.375 | 2.0 |
| 4 | 281496.813 | 1.0 |

Example 10

Live Cell Activation of MMP-2 Activatable Probes In Vitro

Figure 4:
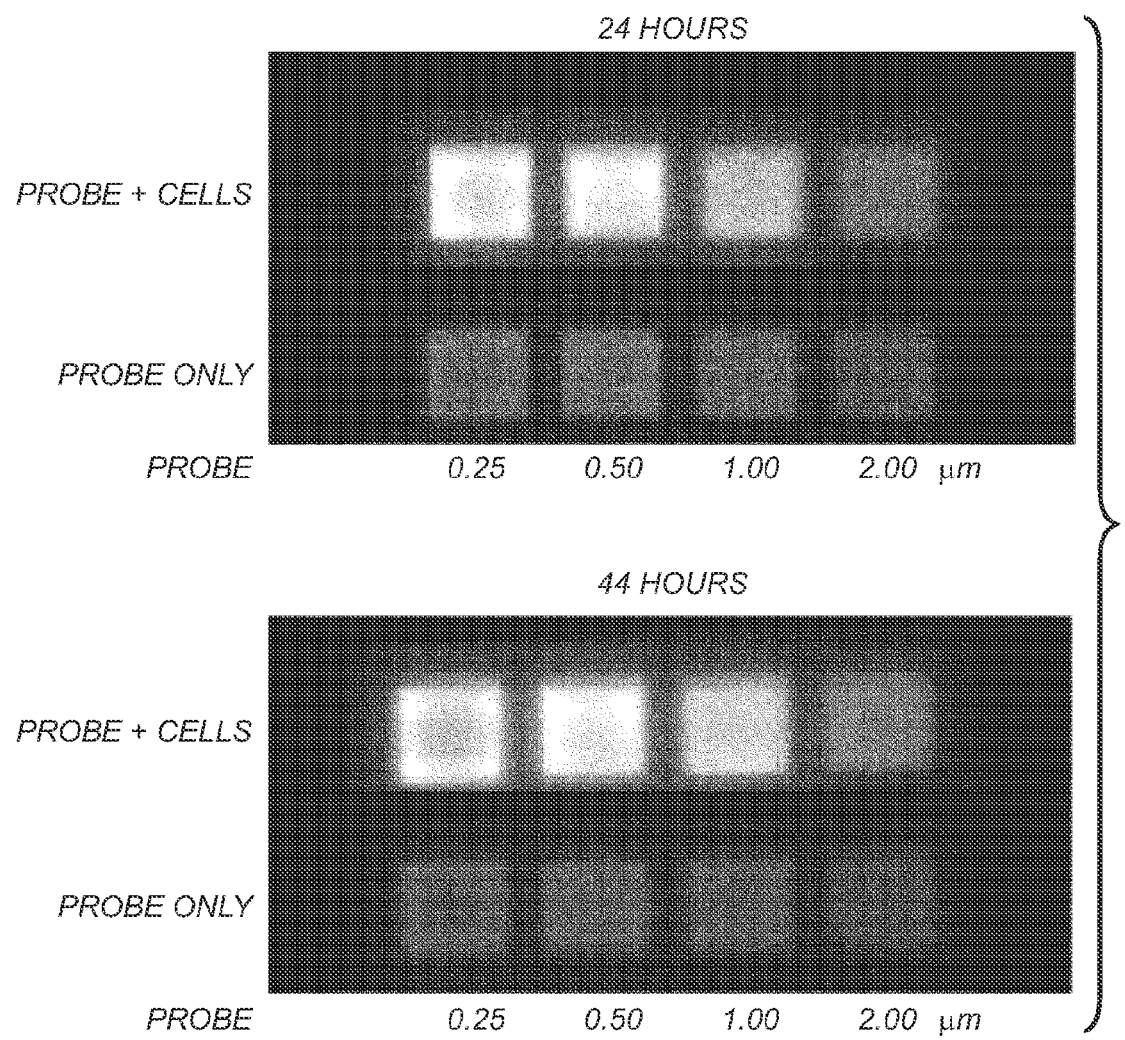
FIG. 4 shows the activation of a fluorescent activatable probe in the presence of HT1080 cancer cells.

HT1080 cancer cells were cultured in each chamber (78000 cells per chamber). Then increasing amounts of activatable probes were added to each chamber and the mixture was incubated for 24 hrs or 44 hrs. Same amount of probes without cells were used as the control. Fluorescence was measured on an Image Station 4000MM. FIG. 4 shows the fluorescence images.

TABLE 5

Data analysis of 24 hr incubation.

| Probe Concentration | Net intensity (arbitrary units) | | Fold Activation |
| --- | --- | --- | --- |
| (μM) | sample | control |  |
| 0.25 | 11330086 | 6849854 | 1.7 |
| 0.5 | 10453644 | 6745129 | 1.5 |
| 1 | 9091127 | 6312944 | 1.4 |
| 2 | 6704315 | 5645303 | 1.2 |

TABLE 6

Data analysis of 44 hr incubation.

| Probe Concentration | Net Intensity (arbitrary units) | | Fold Activation |
| --- | --- | --- | --- |
| (μM) | sample | control |  |
| 0.25 | 10824092 | 5470908 | 2.0 |
| 0.5 | 10966439 | 5515928 | 2.0 |
| 1 | 9370010 | 5279389 | 1.8 |
| 2 | 6765468 | 4640303 | 1.5 |

Example 11

In Vivo Activation of MMP-2 Activatable Probes

Figure 5:
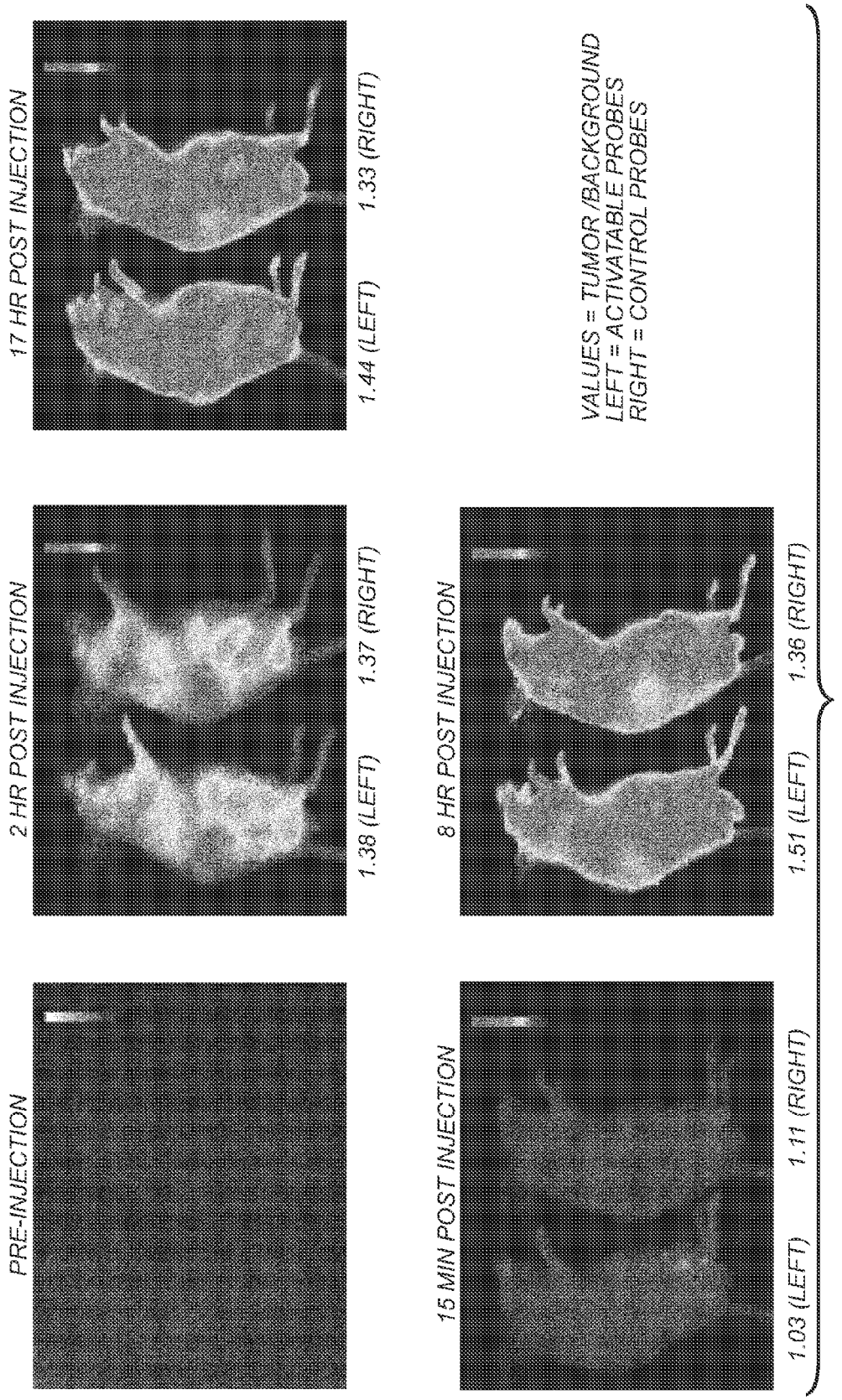
FIG. 5 shows the activation of a 24 nm fluorescent activatable probe in vivo.
Figure 6:
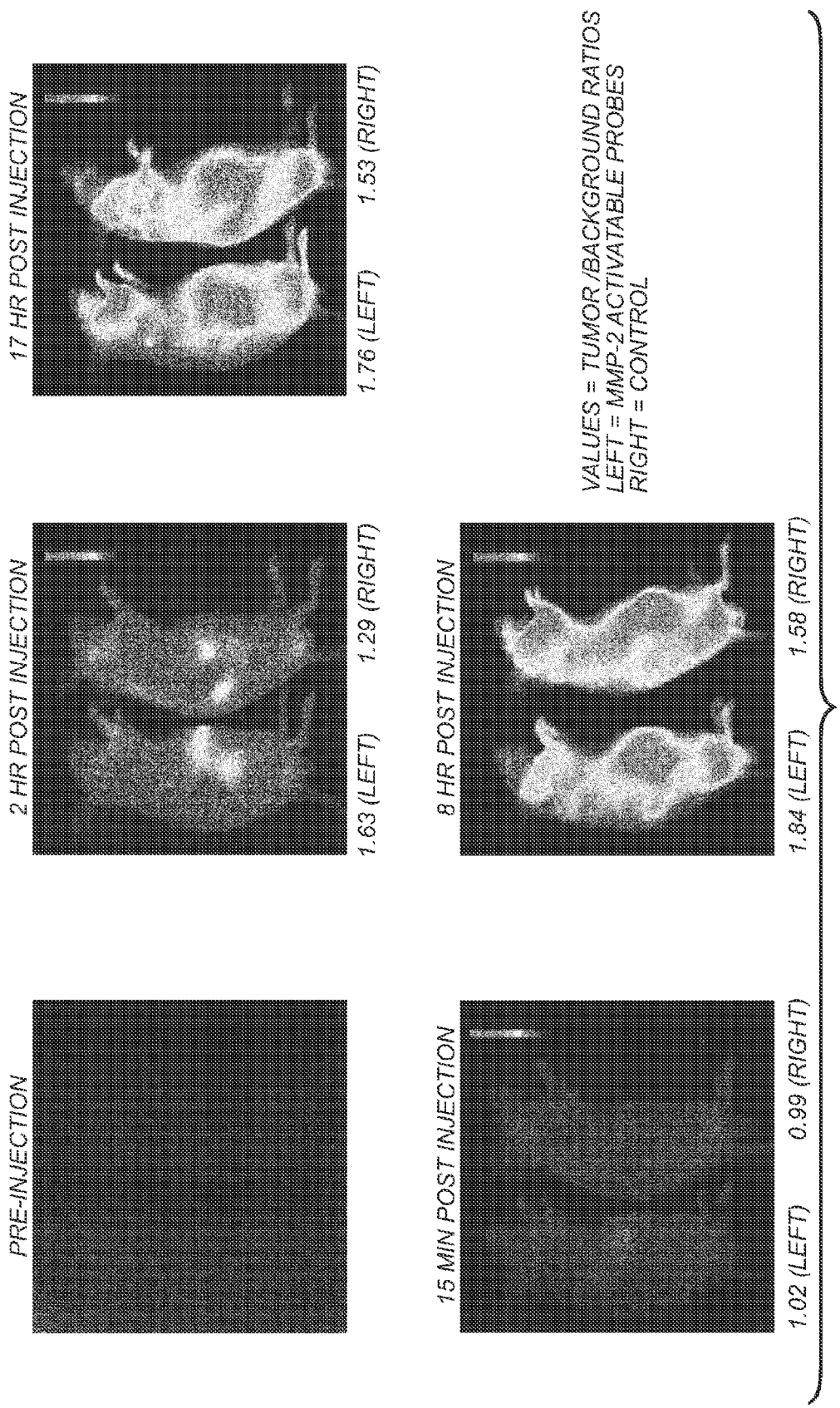
FIG. 6 shows the activation of a 12 nm fluorescent activatable probe in vivo.
Figure 7:
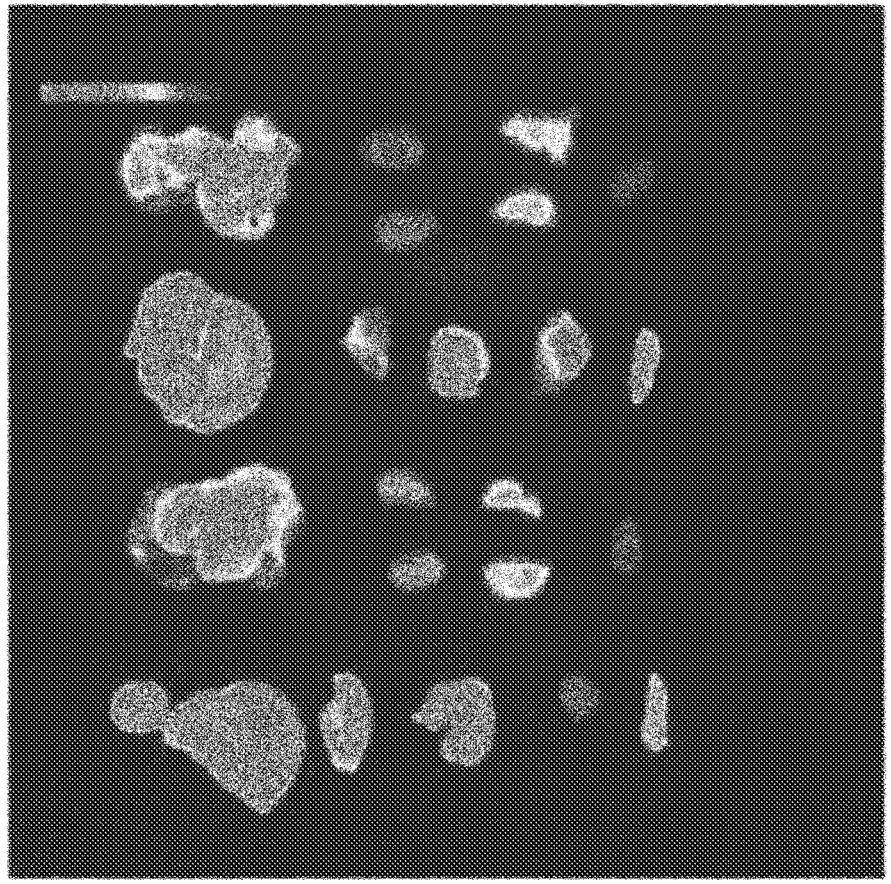
FIG. 7 shows an ex vivo analysis of the activation of a fluorescent activatable probe in vivo.

MMP-2 activatable probes and control probe (constructed using scrambled peptide) based on 12 nm and 24 nm X-sight 761 were synthesized. They were injected i.v. in the mice with large size, mature tumors (HT-1080 cell line). In-vivo imaging was completed pre-injection, 15 min post, 2 hr post, 8 hr post, and 17 hr post. Tumor/Background (T/NT) was performed. The fluorescence was imaged on an In-Vivo Multispectral Imaging System FX. FIG. 5 shows in vivo imaging of mice having tumor injected with 2 nmol of activatable probes and control probes based on 24 nm X-sight 761 at different time points. FIG. 6 shows in vivo imaging of mice having tumor injected with 2 nmol of activatable probes and control probes based on 12 nm X-sight 761 at different time points. FIG. 7 shows ex vivo analysis of organs at 17 hr post for 24 nm nanoparticle based activatable probes and control probes was done. The MMP-2 activatable probes successfully detected the tumor in the mice. The control probes also targeted to the tumor. However, the higher Tumor/Background ratios of activatable probes indicates less non-specific interactions than the control probes. The activatable probes based on the 12 nm X-sight nanoparticles showed higher Tumor/background ratio than the activatable probes based on the 24 nm X-sight nanoparticles. The optimal imaging time-point in vivo is 8-17 hrs post injection.
Example 12
Structure of Large Stokes Shift Dyes
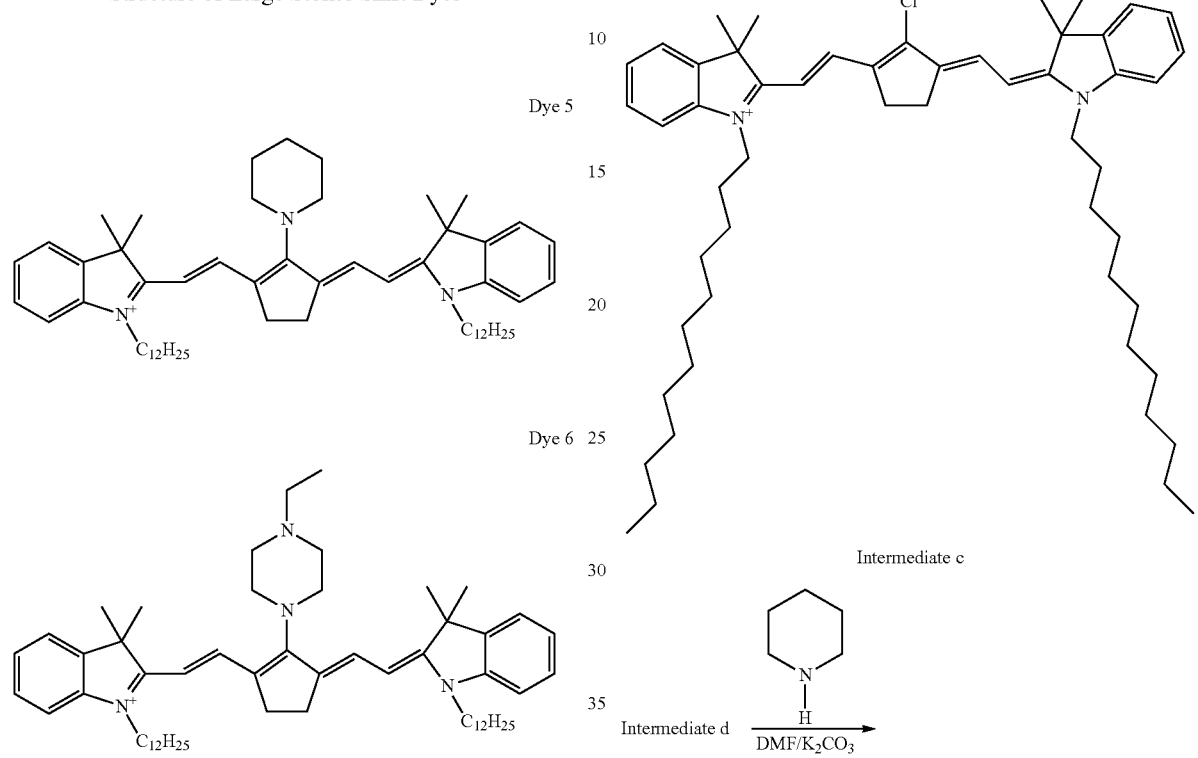
Dye 5
Dye 6
General Synthetic Scheme, Dye 5
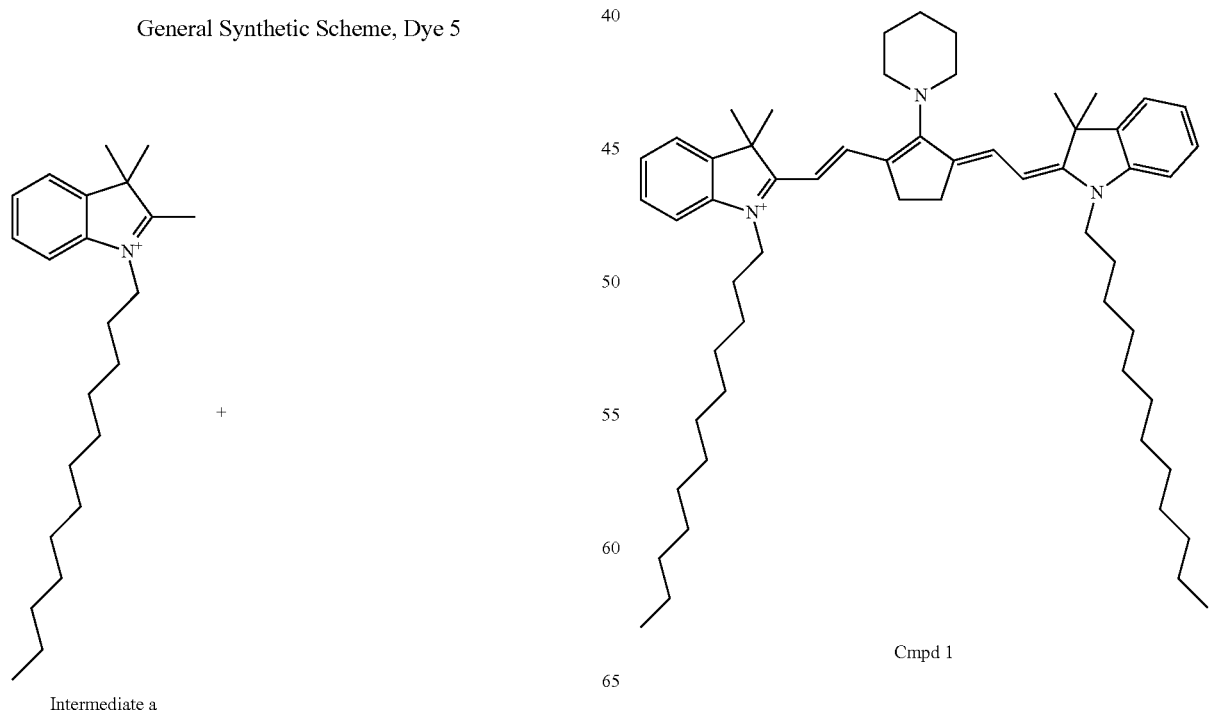
Intermediate a
Intermediate b
Intermediate c
Intermediate d
Cmpd 1

General Synthetic Scheme, Dye 6

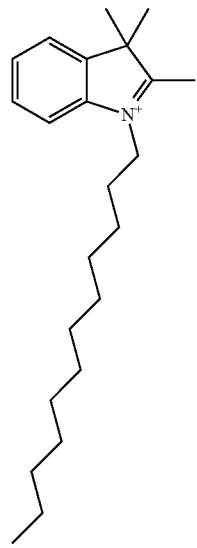

Intermediate a

+

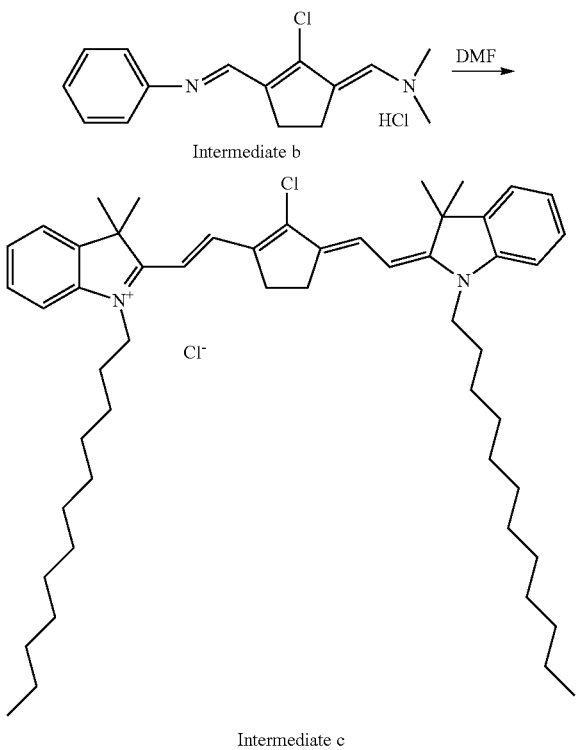

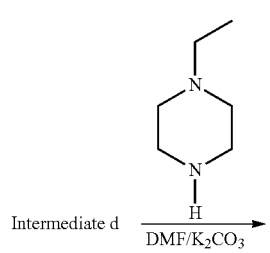

Intermediate d  →  DMF/K₂CO₃

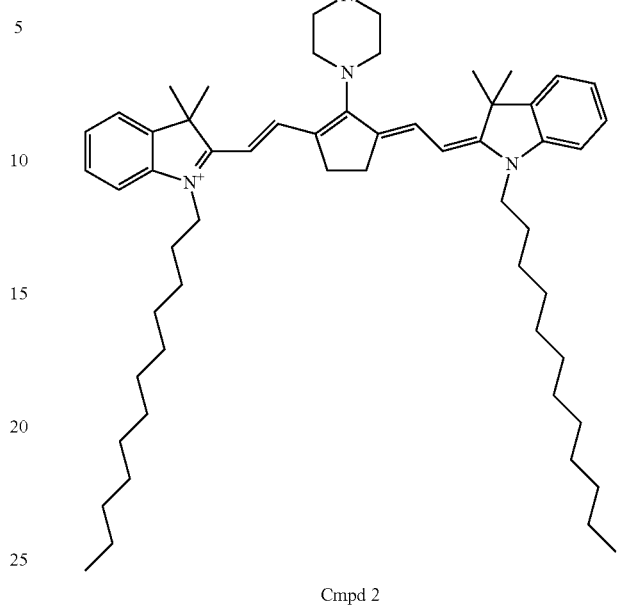

Cmpd 2

Synthetic Procedure 1 for Chloro Intermediate Dye C

This dye was prepared by the procedure above using 2,3,3-trimethyl-1-doceyl-3H-Indolium perchlorate (86 mg, 0.0273 mol) and the dianil (30 mg, 0.0101 mol) in 0.1 mL of acetic anhydride and 1 mL of DMF containing triethylamine (80 µL). The reaction was carried out for 60 minutes at 70° C., cooled to 25° C. and poured into 10 mL of ice water with vigorous stirring. The water was decanted from the oily product then chromatographed on silica gel eluting with 90/10 methylene chloride-methanol. Evaporation of the solvent afforded pure dye (100 mg). Mass spec MW=778.5=M+H$^+$, λmax=780 nm in methanol/H2O (HPLC Diode Array Detector).

Synthesis of Dye 5

This dye was prepared using above chloro dye (50 mg, 0.0615 mmol) and piperidine (28 µL, 20.3 mg, 0.24 mmol) in 0.5 mL of DMF containing triethylamine (80 µL, 0.058 g, 0.58 mmol). The reaction was carried out for 60 minutes at 80° C., cooled to 25° C. and poured into 10 mL of ice water with vigorous stirring. The water was decanted from the oily product then chromatographed on silica gel eluting with 90/10 methylene chloride-methanol. Evaporation of the solvent afforded pure dye (20 mg). Mass Spec=826.6=M+H, λmax=685 nm in methanol (in HPLC/H20 diode array detector).

Synthesis of Dye 6

This dye was prepared using above chloro dye (50 mg, 0.0615 mmol) and N-ethyl-piperazine 29 µL, 26 mg, 0.23 mmol) in 0.5 mL of DMF containing triethylamine (80 µL). The reaction was carried out for 60 minutes at 80° C., cooled to 25° C. and poured into 10 mL of ice water with vigorous stirring. The water was decanted from the oily product then chromatographed on silica gel eluting with 90/10 methylene chloride-methanol. Evaporation of the solvent afforded pure dye (20 mg). Mass Spec=855.7=M+H, λmax=697 nm in methanol (in HPLCdiode array detector).

Example 13

Loading of Particle with Dye 5

A dye solution of ~0.1% was prepared by dissolving 0.0315 g of Dye 5 in 30.545 g of tetrahydrofuran. A 3.2378 g portion of the dye solution was added to a glass vial, followed by 10.5489 g of particle solution from Example 2. The tetrahydrofuran was removed with a small stream of nitrogen over a period of 8-24 hours with stirring. A blue loaded latex LL-1A of 4.27% solids was afforded. Three additional samples with higher loading levels (LL-1B, 1C, 1D) were prepared in an identical manner using the reagent quantities in the table below.

| | | Ex/Em: 703 nm/802 nm | | | |
|---|---|---|---|---|---|
| Loaded latex designation | Dye solution (g) | Nanolatex (g) | Final weight (g) | Conc. Dye in solid latex (mol/L) | Final % solids (% w/w) |
| LL-1A | 3.2378 | 10.5489 | 8.5368 | $4.19 \times 10^{-4}$ | 4.27 |
| LL-1B | 4.6524 | 10.1257 | 8.8755 | $5.78 \times 10^{-4}$ | 4.10 |
| LL-1C | 6.2478 | 10.1725 | 9.0253 | $7.65 \times 10^{-4}$ | 3.95 |
| LL-1D | 7.7532 | 10.2548 | 8.9852 | $9.66 \times 10^{-4}$ | 4.05 |

Example 14

Loading of Particle with Dye 6

A dye solution of ~0.1% was prepared by dissolving 0.0318 g of Dye 6 in 30.653 g of tetrahydrofuran. A 3.0378 g portion of the dye solution was added to a glass vial, followed by 10.3289 g of particle solution from Example 2. The tetrahydrofuran was removed with a small stream of nitrogen over a period of 8-24 hours with stirring. A blue loaded latex LL-2A of 4.00% solids was afforded. One additional sample (LL-2B) was prepared in an identical manner using the reagent quantities in the table below.

| | | Ex/Em: 711 nm/778 nm | | | |
|---|---|---|---|---|---|
| Loaded latex designation | Dye solution (g) | Nanolatex (g) | Final weight (g) | Conc. Dye in solid latex (mol/L) | Final % solids (% w/w) |
| LL-2A | 3.2596 | 10.1023 | 8.2538 | $4.58 \times 10^{-4}$ | 4.51 |
| LL-2B | 4.6357 | 10.0676 | 9.0253 | $5.89 \times 10^{-4}$ | 3.92 |

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

What is claimed is:

1. A nanoparticle comprising:
   a monomer represented by formula:

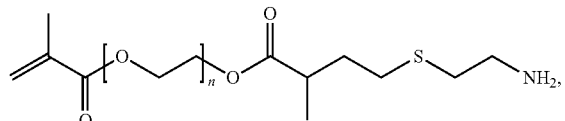

wherein n is 10 to 200;
   at least one cleavable spacer comprising at least one fluorescence activation site, wherein the cleavable spacer is attached at one end to the nanoparticle; and
   at least two dyes of at least two types,
   wherein the at least two types comprise an energy donor type and an energy acceptor type,
   wherein at least one dye of one type is embedded in the nanoparticle and the cleavable spacer has at least one dye of the other type attached, and
   wherein the at least two dyes comprise at least one matched pair capable of fluorescence resonance energy transfer.

2. The nanoparticle of claim 1, wherein the nanoparticle is loaded with the energy donor type of dye, and wherein the dye attached to the cleavable spacer is the energy acceptor type of dye.

3. The nanoparticle of claim 1, wherein the nanoparticle is loaded with the energy acceptor type of dye, and wherein the dye attached to the cleavable spacer is the energy donor type of dye.

4. The nanoparticle of claim 1, wherein the cleavable spacer is selected from the group consisting of DNA, RNA, carbohydrate, amino acid, peptide, protein, polysaccharide, nucleotide, oligonucleotide, nucleic acid, lipid, phospholipids, lipoprotein, and lipopolysaccharide.

5. The nanoparticle of claim 1, wherein the fluorescence activation site can be cleaved by a protease.

6. The nanoparticle of claim 5, wherein the protease is selected from the group consisting of trypsin, cathepsin D, cathepsin B, cathepsin H, cathepsin L, cathepsin S, urokinase, thrombin, plasmin, plasminogen activator, prostate specific antigen, a matrix metalloproteinase (MMP), a kallikrein, a human kallikrein, or human kallikrein 3, a caspase, a caspase 3, a caspase 8, a granzyme B, a calpain.

7. The nanoparticle of claim 1, wherein the energy acceptor type of dye comprises one of the following:
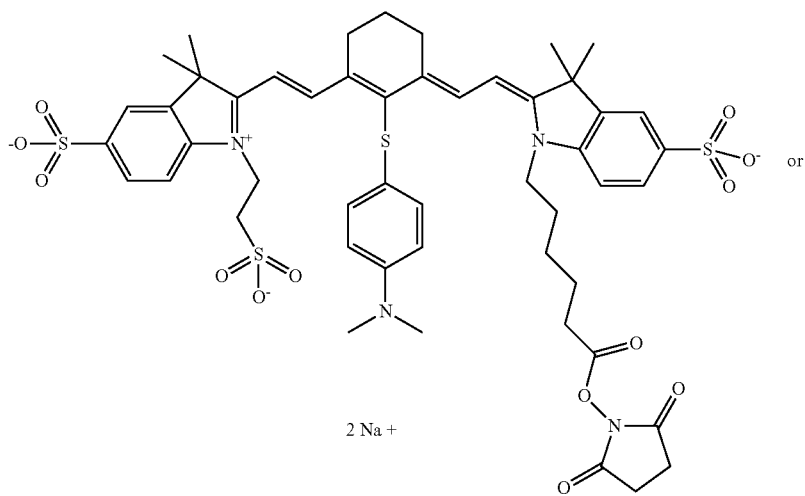
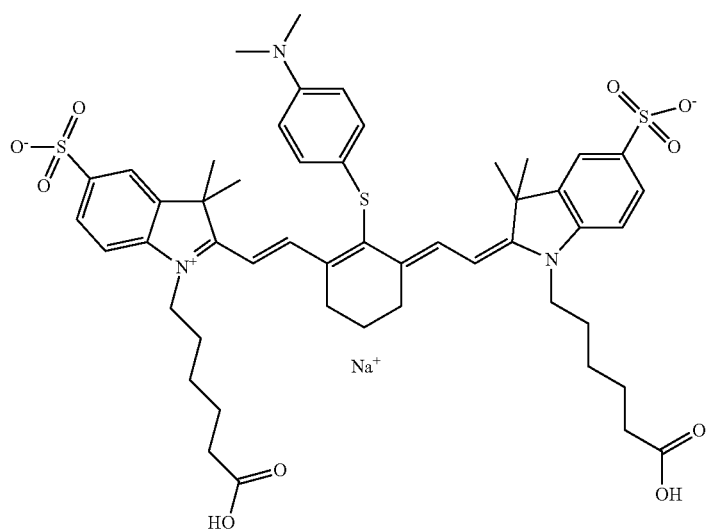
8. The nanoparticle of claim 1, wherein the energy donor type of dye is selected from the group consisting of:
-continued
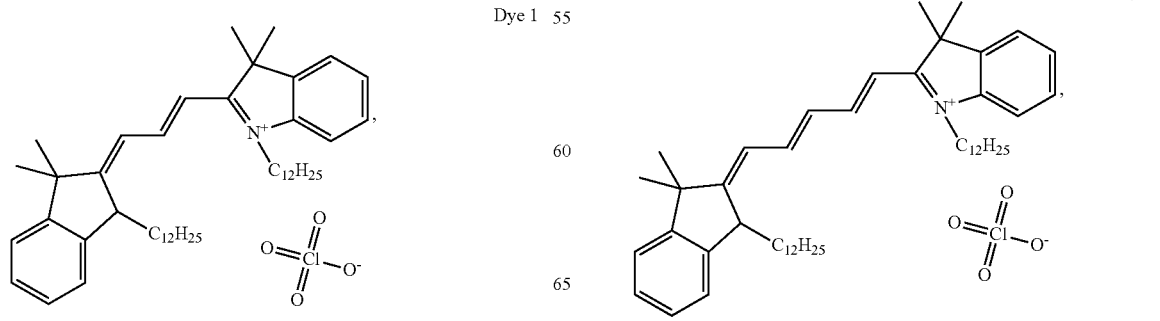

-continued

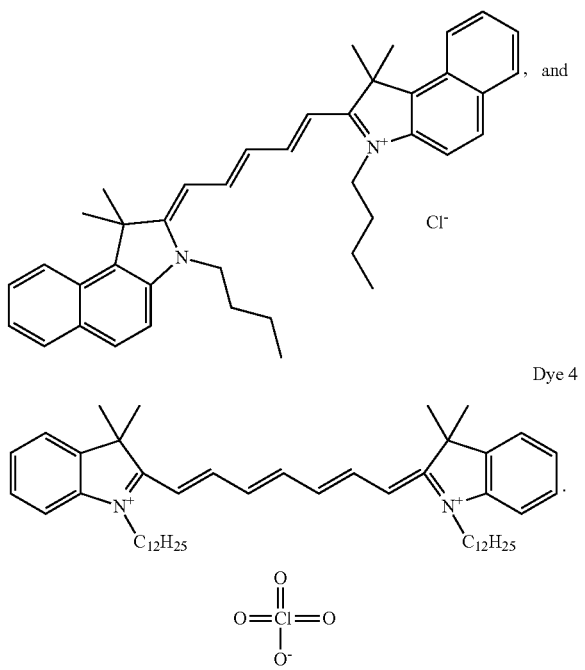

Dye 3, and

Dye 4

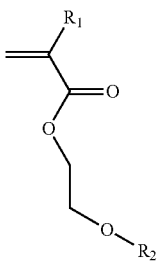

9. The nanoparticle of claim 1, wherein the nanoparticle comprises a latex material, wherein the latex material comprises, a mixture represented by formula: (X)m-(Y)n-(Z)o-(W)p, wherein Y is at least one monomer with at least two ethylenically unsaturated chemical functionalities; Z is at least one polyethylene glycol macromonomer with an average molecular weight of between 300 and 10,000; W is an ethylenic monomer different from X, Y, or Z; and X is at least one water insoluble, alkoxethyl containing monomer represented by formula:

wherein R1 is a radical chosen from the group consisting of methyl and hydrogen, and R2 is a radical chosen from the group consisting of an alkyl group and an aryl group; and m, n, o, and p are weight percent ranges of each component monomer, wherein m ranges between 40-90 percent by weight, n ranges between 1-10 percent by weight, o ranges between 20-60 percent by weight, and p is up to 10 percent by weight.

10. The nanoparticle of claim 1, further comprising a biotargeting moiety comprising an antibody.

11. The nanoparticle of claim 1, wherein the at least one of the dyes is a large Stokes shift dye.

12. The nanoparticle of claim 1, wherein the dye of the energy donor type is a molecular dye.

13. The nanoparticle of claim 1, wherein the dye of the energy acceptor type is a molecular dye or a gold cluster.

14. The nanoparticle of claim 1, wherein the dye of the energy acceptor type is a carbon nanotube or nanoparticles dyed with light absorbing molecules.

15. A method for detecting the presence of an enzyme, comprising:
    contacting a sample with a nanoparticle including a monomer represented by formula:

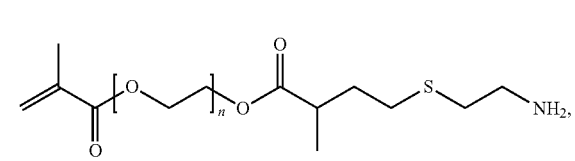

wherein n is 10 to 200, at least one cleavable spacer comprising at least one fluorescence activation site, wherein the cleavable spacer is attached at one end to the nanoparticle, and at least two dyes of at least two types, wherein the two types comprise an energy donor type and an energy acceptor type, wherein at least one dye of one type is embedded in the nanoparticle and the cleavable spacer has at least one dye of the other type attached, and wherein the at least two dyes comprise at least one matched pair capable of fluorescence resonance energy transfer; and
    detecting fluorescence.

16. The method of claim 15, wherein the nanoparticle is loaded with the energy donor type of dye, and wherein the dye attached to the cleavable spacer is the energy acceptor type of dye.

17. The method of claim 15, wherein the nanoparticle is loaded with the energy acceptor type of dye, and wherein the dye attached to the cleavable spacer is the energy donor type of dye.

18. The method of claim 15, wherein the cleavable spacer is selected from the group consisting of DNA, RNA, carbohydrate, amino acid, peptide, protein, polysaccharide, nucleotide, oligonucleotide, nucleic acid, lipid, phospholipids, lipoprotein, and lipopolysaccharide.

19. The nanoparticle of claim 15, wherein the fluorescence activation site can be cleaved by a protease.

20. A method for detecting the presence of an enzyme, comprising:
    administering to a mammal a nanoparticle including a monomer represented by formula:

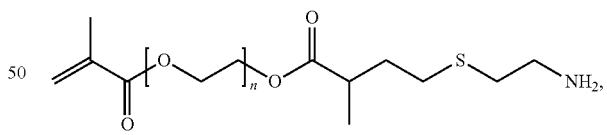

wherein n is 10 to 200, at least one cleavable spacer comprising at least one fluorescence activation site, wherein the cleavable spacer is attached at one end to the nanoparticle, and at least two dyes of at least two types, wherein the at least two types comprise an energy donor type and an energy acceptor type, wherein at least one dye of one type is embedded in the nanoparticle and the cleavable spacer has at least one dye of the other type attached, and wherein the at least two dyes comprise at least one matched pair capable of fluorescence resonance energy transfer; and
    detecting fluorescence.

* * * * *